US010953181B2

(12) United States Patent
Hallett et al.

(10) Patent No.: US 10,953,181 B2
(45) Date of Patent: Mar. 23, 2021

(54) RESPIRATORY MASK

(71) Applicant: Ventific Holdings Pty Ltd., New South Wales (AU)

(72) Inventors: Michael Hallett, New South Wales (AU); Roger Foote, New South Wales (AU); Allan Gregersen, Auckland (NZ); Michael Gunaratnam, New South Wales (AU)

(73) Assignee: Ventific Holdings Pty Ltd., Chatswood (AU)

( * ) Notice: Subject to any disclaimer, the term of this patent is extended or adjusted under 35 U.S.C. 154(b) by 361 days.

(21) Appl. No.: 15/578,587

(22) PCT Filed: Jun. 9, 2016

(86) PCT No.: PCT/AU2016/050467
§ 371 (c)(1),
(2) Date: Nov. 30, 2017

(87) PCT Pub. No.: WO2016/197195
PCT Pub. Date: Dec. 15, 2016

(65) Prior Publication Data
US 2018/0133426 A1 May 17, 2018

(30) Foreign Application Priority Data
Jun. 11, 2015 (AU) .................. 2015902346

(51) Int. Cl.
*A61M 16/06* (2006.01)
*A61M 16/10* (2006.01)
(Continued)

(52) U.S. Cl.
CPC .......... *A61M 16/065* (2014.02); *A61M 16/06* (2013.01); *A61M 16/0644* (2014.02);
(Continued)

(58) Field of Classification Search
CPC ............ A61M 16/065; A61M 16/0644; A61M 16/06; A61M 16/0683; A61M 16/0816
See application file for complete search history.

(56) References Cited

U.S. PATENT DOCUMENTS 6,789,543 B2 * 9/2004 Cannon ............. A61M 16/0683
128/206.18
7,318,439 B2 * 1/2008 Raje ..................... A61M 16/08
128/206.24
(Continued)

FOREIGN PATENT DOCUMENTS

| AU | 2014204441 A1 | 7/2014 |
| EP | 2005986 A2 | 12/2008 |
| WO | 2011/110968 A2 | 9/2011 |

OTHER PUBLICATIONS

PCT/AU2016/050467 International Search Report dated Sep. 6, 2016.

*Primary Examiner* — Kendra D Carter
*Assistant Examiner* — Thao Tran
(74) *Attorney, Agent, or Firm* — Wagenknecht IP Law Group, PC

(57) ABSTRACT

The invention provides a respiratory mask comprising a mask body including a base and walls upstanding from the base and converging towards an apical region and a forehead engagement member extending from the apical region of the mask body. The forehead engagement member coupled to the mask body so as to be movable relative to the mask body in a sagittal plane when the mask body is worn by a patient. An adjustment mechanism is provided for adjusting the relative positions of the forehead engagement member and the mask body. In another aspect, the invention also provides a respiratory mask including a mask body including a base and walls upstanding from the base and converging towards an apical region. The body includes a pair of transversely (Continued)

opposite headgear anchors adapted for attachment to headgear that a patient wears during use to secure the mask to the face of a patient.

16 Claims, 11 Drawing Sheets

(51) Int. Cl.
  *A61M 16/00* (2006.01)
  *A61M 16/08* (2006.01)
  *A61M 16/12* (2006.01)
(52) U.S. Cl.
  CPC .... *A61M 16/0683* (2013.01); *A61M 16/1045* (2013.01); *A61M 16/0816* (2013.01); *A61M 16/125* (2014.02); *A61M 2016/0027* (2013.01); *A61M 2202/0208* (2013.01); *A61M 2205/3368* (2013.01)

(56) References Cited

U.S. PATENT DOCUMENTS

| | | | | |
|---|---|---|---|---|
| 8,327,850 B2* | 12/2012 | Ng | ............... | A61M 16/06 128/206.24 |
| 8,490,623 B2* | 7/2013 | Berthon-Jones | ............... | A61M 16/0633 128/206.21 |
| 8,720,443 B2* | 5/2014 | Kooij | ............... | A61M 16/06 128/207.11 |
| 9,572,947 B2* | 2/2017 | Grashow | ............... | A61M 16/0622 |
| 9,669,178 B2* | 6/2017 | Rothermel | ............... | A61M 16/0875 |
| 9,775,961 B2* | 10/2017 | Zeijlstra | ............... | A61M 16/0644 |
| 9,795,755 B2* | 10/2017 | Zeijlstra | ............... | A61M 16/0622 |
| 2004/0025883 A1* | 2/2004 | Eaton | ............... | A61M 16/0683 128/206.27 |
| 2004/0045551 A1* | 3/2004 | Eaton | ............... | A61M 16/06 128/206.21 |
| 2005/0072428 A1* | 4/2005 | Ho | ............... | A61M 16/06 128/205.25 |
| 2005/0076913 A1* | 4/2005 | Ho | ............... | A61M 16/06 128/206.27 |
| 2006/0076019 A1* | 4/2006 | Ho | ............... | A61M 16/06 128/206.24 |
| 2007/0028919 A1* | 2/2007 | Ho | ............... | A61M 16/0633 128/204.18 |
| 2008/0053446 A1* | 3/2008 | Sleeper | ............... | A61M 16/06 128/205.25 |
| 2010/0108069 A1* | 5/2010 | Chang | ............... | A61M 16/06 128/205.25 |
| 2011/0126838 A1* | 6/2011 | Alberici | ............... | A61M 16/0638 128/207.11 |
| 2012/0138061 A1* | 6/2012 | Dravitzki | ............... | A61M 16/0622 128/205.25 |
| 2015/0075534 A1* | 3/2015 | Gulliver | ............... | A42B 3/08 128/207.13 |
| 2015/0328421 A1* | 11/2015 | Stephenson | ............... | A61M 16/06 128/205.25 |
| 2016/0339195 A1* | 11/2016 | Raje | ............... | A61M 16/0875 |
| 2017/0368288 A1* | 12/2017 | Stephens | ............... | A61M 16/06 |
| 2018/0250485 A1* | 9/2018 | Zhan | ............... | A61M 16/0638 |

* cited by examiner

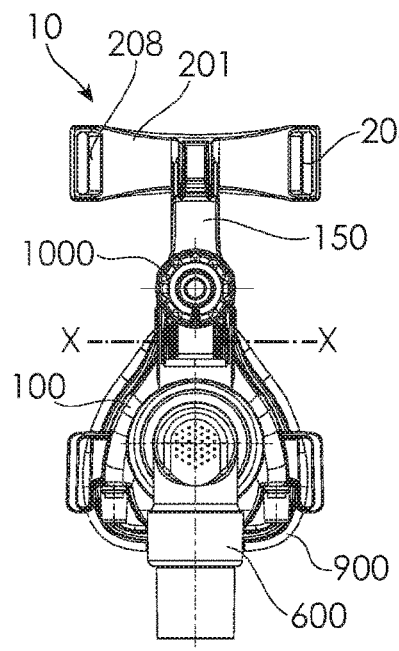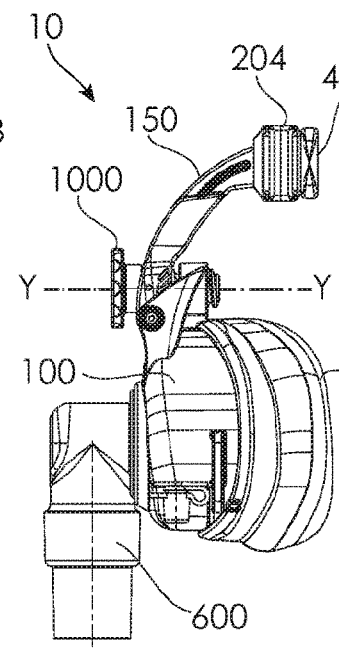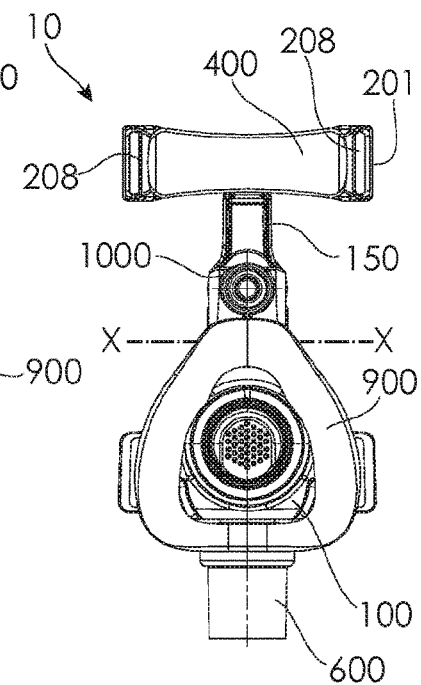
Fig. 5      Fig. 6      Fig. 7
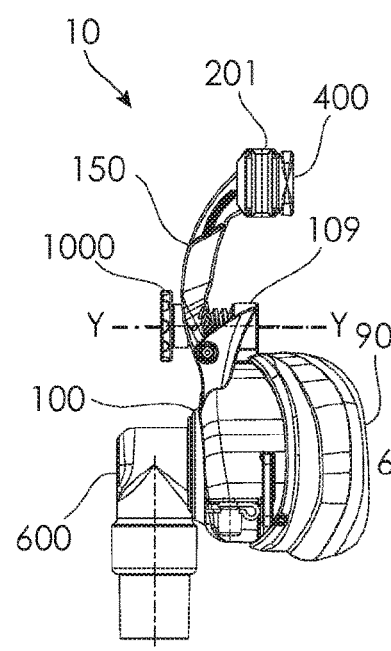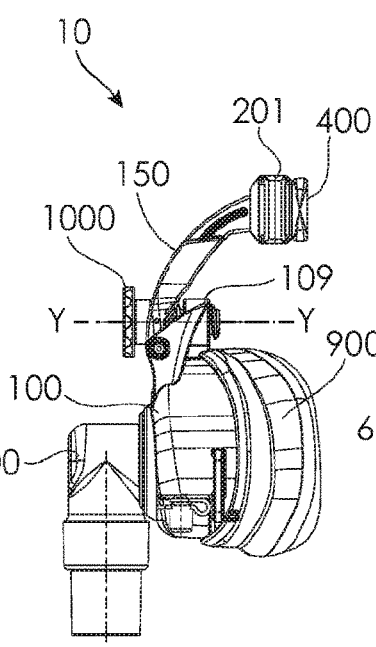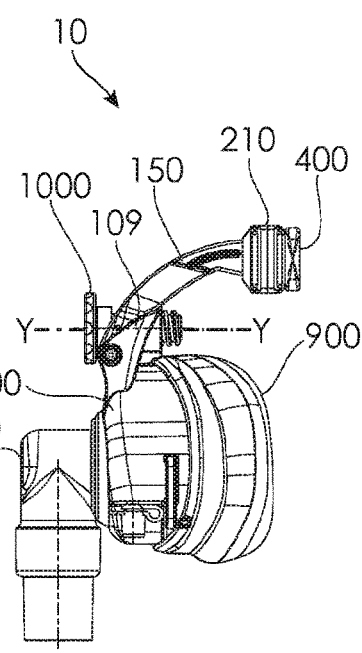
Fig. 8      Fig. 9      Fig. 10

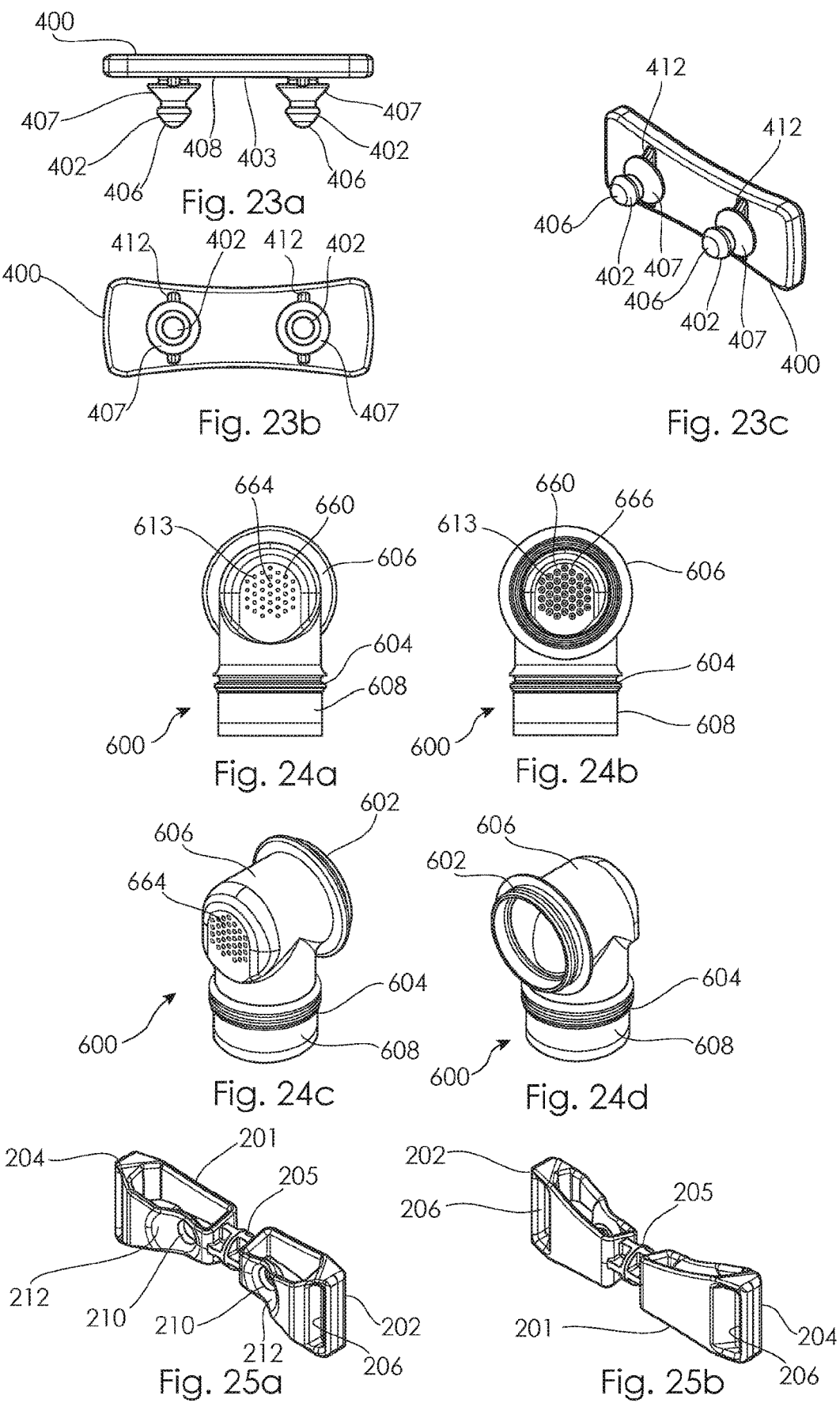

RESPIRATORY MASK

CROSS REFERENCE TO RELATED APPLICATIONS

This is a US national phase application under 35 USC § 371 of international patent application no. PCT/AU2016/050467, filed Jun. 9, 2016, which itself claims priority to Australian application no. 2015902346, filed Jun. 11, 2015. Each of the applications referred to in this paragraph are herein incorporated by reference in their entireties.

FIELD OF THE INVENTION

The present disclosure relates to a mask adapted for the delivery of gas to a patient for the treatment of respiratory or sleeping disorders. The present disclosure may be suitable for use with Continuous Positive Airway Pressure (CPAP), Non-invasive Positive Pressure Ventilation (NIPPV), ventilators or Variable Positive Airway Pressure (VPAP) devices.

BACKGROUND

Respiratory masks used in the treatment of sleep disordered breathing (SDB) may comprise either a nasal mask, designed to cover a patients nose, or a full face mask designed to cover the nose and mouth of the patient. A cushion is commonly used with the mask and comfortably spaces the rigid shell away from the face, while also forming a gas tight seal. In addition, the mask is commonly secured to the patients face by a strap or system of straps/headgear which extends around the rear of the patient's head. The tension in these straps is then adjusted to secure the mask against the patients face with sufficient force to achieve a gas tight seal there-between.

Gas is supplied to the mask by a blower and is directed to the mask through a conduit or tube. The mask system typically further includes a means such as vent holes for releasing exhaled $CO_2$ and also typically includes ports through which mask pressure may be measured and/or supplemental oxygen supply may be delivered to the patient.

Existing masks can include forehead supports for providing a support outside the sealing boundary of the mask seal or cushion to limit the force applied to seal the cushion onto the patients face in the pressure sensitive nasal bridge area. Historically, the most basic forms of forehead support took the form of flat sign-post like structures with a single pad attached to comfortably contact with the patient's forehead, and slots to receive the headgear. The pad would be selected from a range of pads of varying thickness and attached by adhesive to the rigid forehead support post. Whilst effective, the trial and error process required to select the correct pad and finally attach it to the mask is a cumbersome and time consuming solution for achieving the desired forehead support offset.

Existing masks exist that include quick release clips for attaching the headgear straps to the mask body. These clips may take the form of a seatbelt buckle configuration whereby the trailing portion of the clip has a slot to receive the headgear strap and the leading portion has a resiliently biased button or buttons which engage with an aperture in the mask when inserted and which release when pressed into disengagement by the user. Other existing clips comprise a hooked leading portion which detents into a corresponding recess in the mask or vice versa, along with the trailing slot to receive the headgear. Shortcomings of this style of clip include difficulty in operating them by feel in the dark.

Any discussion of background art throughout the specification should in no way be considered as an admission that any of the documents or other material referred to was published, known or forms part of the common general knowledge.

SUMMARY OF THE INVENTION

In one aspect, the present invention provides a respiratory mask, comprising: a mask body including a base and walls upstanding from the base and converging towards an apical region; a forehead engagement member extending from the apical region of the mask body; the forehead engagement member coupled to the mask body so as to be movable relative to the mask body in a sagittal plane when the mask body is worn by a patient; and an adjustment mechanism for adjusting the relative positions of the forehead engagement member and the mask body.

In embodiments, the forehead engagement member includes an arm extending from the apical region of the mask body to a forehead region of a patient when in-use, the adjustment mechanism being operable to adjust the relative positions of the arm and the mask body.

Preferably, the arm is pivotally coupled to the mask body at the apical region of the mask body and the adjustment mechanism is located in the region of the pivotal coupling between the arm and the apical region of the mask body.

The adjustment mechanism can include a manually operable member that is adapted for movement in an axial direction relative to the mask body.

In embodiments, a portion of the forehead engagement member is captured by the manually operable member whereby movement of the manually operable member in the axial direction relative to the mask body adjusts the position of the forehead engagement member relative to the mask body.

Preferably, the manually operable member includes a threaded shaft that is threadably coupled to a threaded aperture at the apical region of the mask body. In an embodiment, the threaded shaft includes a knurled head.

In embodiments, a distal end of the arm is pivotally coupled to a forehead support member for pivotal movement of the forehead support member relative to the arm.

Preferably, the forehead support member comprises a forehead cushion removably coupled thereto for contacting a patients forehead wherein a main body of the forehead cushion is supported in spaced apart relation to the forehead support member.

Preferably, the mask body includes a pair of gas ports that are disposed in outwardly and downwardly facing recesses on laterally opposite sides within the base of the mask body.

Each of the gas ports can include a spigot extending downwardly within a respective one of the recesses. Each spigot can include an axial lumen for fluid communication between an internal cavity of the mask body and a conduit coupled to the spigot.

Preferably, an elbow shaped swivel gas conduit extends from a front of the mask body and includes a vent array comprising a plurality of vent holes tapering from a larger diameter proximal opening to a smaller diameter distal opening. Alternatively, or additionally, the mask body may include the vent array.

In embodiments of the above aspect, the body preferably includes a pair of transversely opposite headgear anchors adapted for attachment to headgear that a patient wears during use to secure the mask to the patients face.

In another aspect, the present invention provides a respiratory mask, comprising: a mask body including a base and walls upstanding from the base and converging towards an apical region; and a pair of transversely opposite headgear anchors adapted for attachment to headgear that a patient wears during use to secure the mask to the patients face. Accordingly, in this aspect of the invention, the respiratory mask omits the forehead engagement member of the above described aspect of the invention and embodiments thereof.

The following discussion embodiments of the headgear anchors relate to embodiments of either of the above aspects including and not including the forehead engagement member.

Each of the headgear anchors can include an aperture adapted for receiving and retaining a headgear coupling or a loop of textile headgear material.

Each of the headgear anchors can be adapted for snap fit engagement with a headgear coupling.

In embodiments, the headgear anchor includes a shaft having a proximal end near to the mask body and a distal end projecting away from the mask body, the shaft member including a radially outwardly facing slot adapted to receive a portion of a headgear coupling.

Preferably, the radially outwardly facing slot is annular and canted and is defined by a proximal canted annular ridge and an axially spaced apart and canted annular distal ridge.

Preferably, the headgear coupling includes an aperture adapted to receive the headgear anchor and a resiliently displaceable engagement member within the aperture adapted to engage the headgear coupling.

The resiliently displaceable engagement member can include one or more radially inwardly extending ramps supported within the aperture by resiliently flexible support members adapted to bias the ramps in a radially inwards direction.

In embodiments of either of the aspects disclosed above, the respiratory mask further includes a heat and moisture exchanger removably locatable within a cavity defined within the mask body.

Preferably, the heat and moisture exchanger includes a removable cartridge comprising a heat and moisture exchanger element captured between a body portion of the cartridge and a removable web.

Embodiments of the present invention may provide a more comfortable mask device for the delivery of breathable gas to a patient, a more suitable adjustment means for positioning a mask onto a patient's face or a useful alternative. Embodiments of the present invention may reduce fluid loss or assist in retaining fluids of a patient during use. Embodiments of the present invention may increase compliance with an air pressure therapy or provide a device which is a useful alternative.

BRIEF DESCRIPTION OF THE FIGURES

The invention will now be described in more detail with reference to embodiments of the invention illustrated in the accompanying drawings, wherein:

FIGS. 5, 6 and 7 illustrate front, side and rear views of the mask of FIG. 1;

FIG. 8 illustrates a side view of the mask of FIG. 1 wherein the forehead support, in particular the arm and the forehead support member and forehead cushion are in a forward position relative to a patient's face wearing the mask;

FIG. 9 illustrates a side view of the mask of FIG. 1 wherein the forehead support is adjusted to an intermediate position;

FIG. 10 illustrates a side view of the mask of FIG. 1 wherein the forehead support is adjusted to a rearward position;

FIGS. 23a, 23b and 23c illustrate top, front and perspective views of a forehead cushion of the masks of FIGS. 1, 11, 12 and 20;

FIGS. 24a, 24b, 24c and 24d illustrate front and rear views and forward and rearward perspective views of an elbow or swivel of the mask of FIGS. 1 and 11;

FIGS. 25a and 25b illustrate rear and front perspective views of the forehead support member of the mask of FIG. 1;

DETAILED DESCRIPTION

FIGS. 1 to 10 illustrate an embodiment of the invention including a mask 10 with a mask body 100 formed as a moulded shell of polymer such as polycarbonate, acrylonitrile butadiene styrene (ABS), polysulfone (PSU), acrylic based polymers such as CYROLITE+, or any suitable rigid polymers or polymer blends. Other components of the mask are attached to the body 100 as will be described herein. Optionally, the mask body 100 may be formed from two or more pieces. The mask 10 may be adapted for use with Continuous Positive Airway Pressure (CPAP) or Non-invasive Positive Pressure Ventilation (NIPPV) devices. Preferably, the mask 10 is a nasal mask 10 which substantially covers the nasal region of a patient, in use. In alternate embodiments the mask 10 may be a full face mask (not shown) which substantially covers the nose and the mouth regions of a patient.

Figure 1:
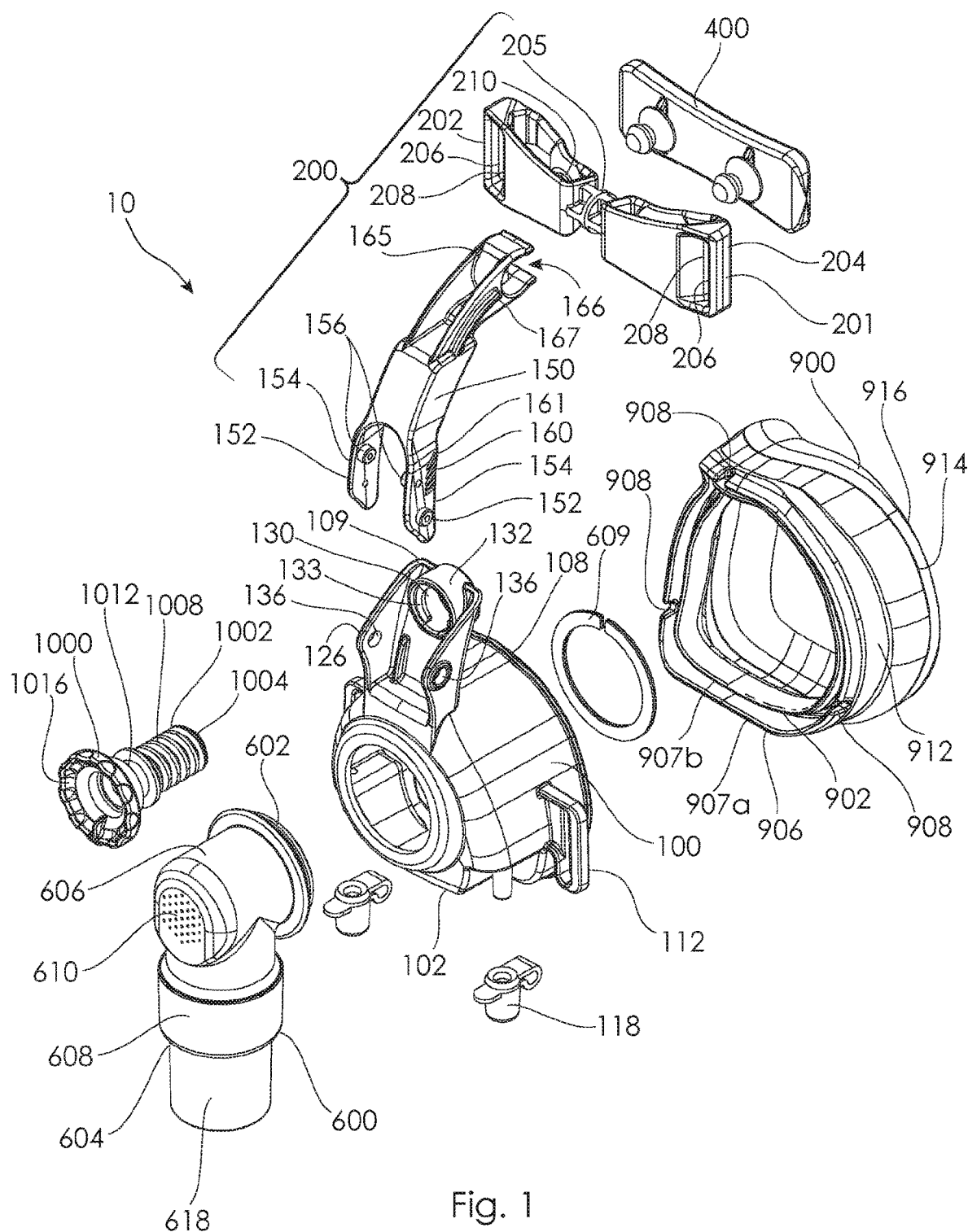
FIG. 1 illustrates an exploded perspective view of a mask in accordance with an embodiment of the invention.
Figures 2, 3:
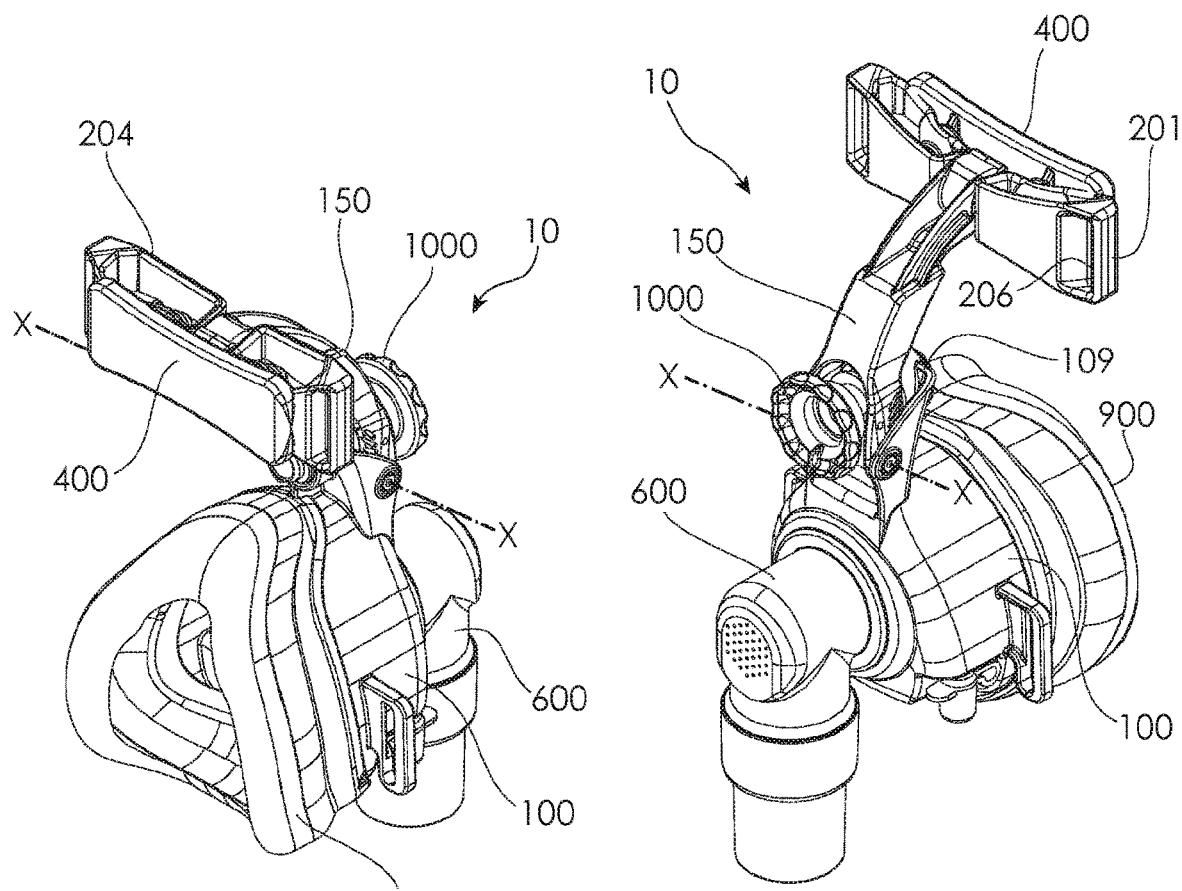
FIG. 2 illustrates a rearward perspective view of the mask of FIG. 1.
FIG. 3 illustrates a forward perspective view of the mask of FIG. 1.
Figure 4:
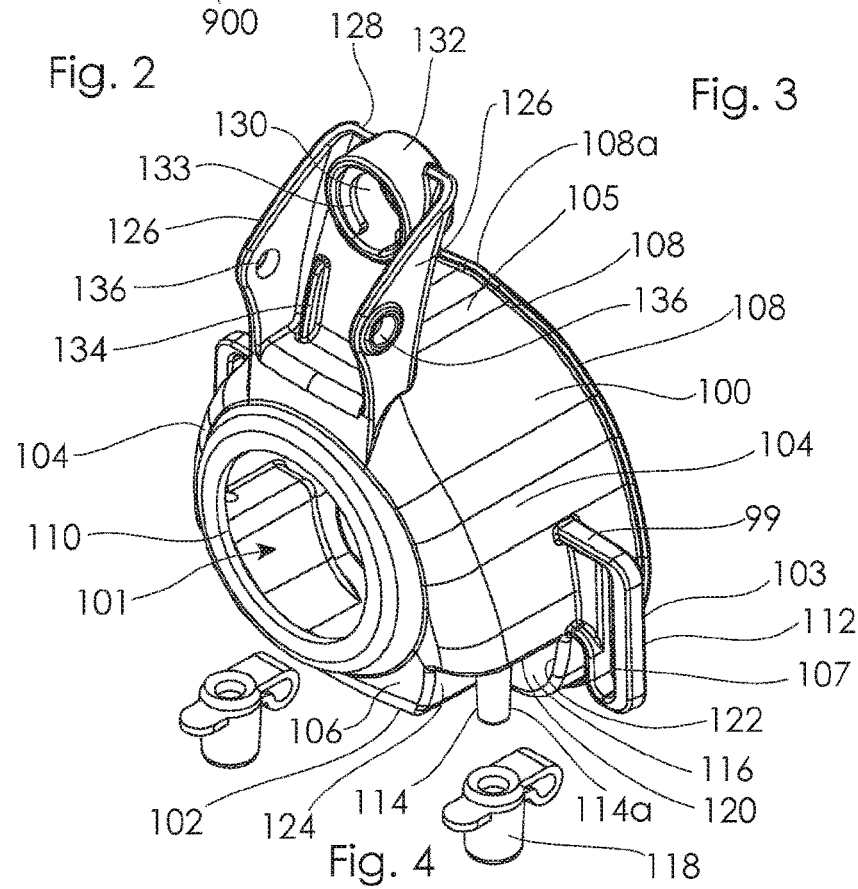
FIG. 4 illustrates a forward perspective view of a mask body of the mask of FIG. 1.

FIGS. 11, 12 to 19, 20 to 22, 26 to 30 and 31 to 33 illustrate further embodiments of the mask 310, 410, 510, 610, 710 in which the features of the masks 310, 410, 510, 610, 710 are similar to the mask 10 of FIGS. 1 to 10. Differences between the embodiments are described in detail below and include different headgear anchors 312, 412, 512, 712 in the embodiments of FIGS. 11 to 22 and 31 to 33 to the headgear anchor 112 of FIGS. 1 to 10, the inclusion of an HME (heat and moisture exchanger) cartridge 800 comprising an HME housing 802 and HME element 814 in the mask 610 of FIGS. 26 to 30 and a different form of a forehead support 320 in the mask 310 of FIG. 11 to the form of the forehead support 200 of the rest of the embodiments. Accordingly, for the sake of convenience, the embodiment of the mask 10 of FIGS. 1 to 10 will be described in detail below and it shall be assumed that such features are also features of the other embodiments of the mask 310, 410, 510, 610, 710 of FIGS. 11 to 33 unless stated otherwise The body 100 of the mask 10 of FIGS. 1 to 11 includes, as shown in FIGS. 1 and 4 in particular, a generally triangular form that, when viewed from the front includes a lower wall 102 and two side walls 104 upstanding from the lower wall 102 that converge to form an apex 105. A front wall 106 extends between the lower wall 102 and two side walls 104. The lower wall 102, two side walls 104 and front wall 106 define an internal cavity 101 of the mask body 100 that, in use, covers a portion of the patients face including the patients nose, and in a full face mask, mouth. A rim 108 extending substantially around, or completely around, a rearward edge of the side walls 104 and the lower wall 102 is adapted for engaging with a face cushion 900. The rim 108 has an indented or recessed portion 108a at the apex 105 such that, in use, the recessed portion 108a can receive the nasal bridge of the patient. The front wall 106 further comprises a gas inlet aperture 110 generally at the centre of the body 100 for connection of a rotatable connector or elbow or swivel 600 connected to a gas supply conduit (not shown). In alternative embodiments, the gas inlet aperture 110 may be disposed off-centre (not shown) or near to the apex 105 (not shown) of the body 100.

The mask 10 includes two port members 114 that are disposed in recesses 116 near opposing ends of the lower wall 102 of the mask body 100. Each port member 114 is preferably in the form of a tubular spigot 114a. The spigots 114a project downwards and away from the apex 105 of the mask body 100 and have an axial lumen extending therethrough, such that the lumen allows the flow of fluid (preferably gas) between the patient's face and a fluid supply (not shown) when the spigots 114a are in use. The recesses 116 containing the port members 114 are positioned near to, or adjacent to, the headgear anchors 112 and the spigots 114a are tapered such that their distal, free ends are smaller than their proximal ends adjoining the body 100. The positioning of the recesses 116 and the spigots 114a may direct a gas flow through the spigot 114a, such as oxygen, towards the patient's nose or mouth. An external surface of each of the spigots 114a is tapered to allow a pressure tube (not shown) to be urged onto and engage each spigot 114a and form a gastight seal therewith. The tapering of the spigots 114a is preferably about 1 to 3 degrees relative to a longitudinal axis of the lumen of the spigot 114a, or preferably in a range of about 1.5 to 1.8 degrees, or more preferably conforms to Luer design standards. The lumen of the spigot 114a has a substantially uniform diameter to allow a consistent flow of gas through the lumen. The lumen may comprise a slight draft angle or taper of 1 degree or so to facilitate moulding thereof.

The spigots 114a may be used for measuring gas pressure inside the mask 10 during use by allowing for a tube coupled to a pressure measurement device to be engaged therewith. The spigots 114a may be used for provision of a gas flow, such as oxygen, to or from the mask 10 such as by connection of a tube thereto that is coupled to a gas provision or recovery device. The distal end of the spigot 114a is rounded to facilitate an easy engagement of a tube thereto and reduce potential damage to the tube. When the spigots 114a are not in use, they are covered by a sealing cap 118 which may be made of silicone or other resilient material, which is urged onto the spigot 114a such that a gas tight seal is achieved between the sealing cap 118 and the spigot 114a. The bottom of the sealing cap 118 is partially elevated from the bottom of the lower wall 102 of the mask body 100 to minimise interaction with sheets or cushions during use, and to provide a more compact configuration.

The recesses 116 containing the spigots 114a are formed in the mask body 100 so as to be generally trapezoidal in elevation, relative to the lower wall 102, and sealed from the mask cavity 101. The trapezoidal shape of the recesses 116 may improve the structural integrity of the mask body 100 by minimising the number of potential weakness zones formed in the mask body and may improve manufacturing efficiency. Alternatively, the recesses 116 can be formed with a rectangular shape. The recesses 116 allow positioning of each spigot 114a closer to the centre of the mask body 100 such that each spigot 114a does not protrude, or only partially protrudes, past the lower wall 102. The positioning of the spigot 114a within the bounds of the lower wall 102 and side walls 104 and within the recess 116, as illustrated in the embodiment of FIGS. 1 to 10 and in the embodiment of FIG. 11, has a number of advantages, namely minimising stress or strain on the spigot 114a such as might occur with accidental bumping of the mask 10 when worn by a patient, providing unobstructed access to the spigots 114a and minimising interference with the movement of the elbow or swivel 600. The recesses 116 include an upper wall 120 to which the spigot 114a is integrally formed and is generally planar. The spigot 114a extends in a substantially perpendicular and downwards direction relative to the upper wall 120. Each recess is bounded by the upper wall 120 as well as a recess rear wall 122 and a recess side wall 124 and is open at the bottom, front and to one side. Having an open front and side is advantageous as this allows ease of placement of a tube on the spigot 114a. Corners and edges of the recess 116, between the rear wall 122, side wall 124 and upper wall 120, may be rounded to minimise stress zones or weakness zones forming in the mask thus providing a more resilient mask body 100.

The spigots 114a may optionally be connected, via a tube, to a manometer for measuring pressure within the mask cavity during use. Alternatively, the spigots 114a may be used in communication with transducers or a device employing control algorithms to manipulate operation of the device to automatically or adaptively adjust the device to increase compliance of a patient to a prescribed therapy. While the spigot 114a is illustrated with a Luer slip type configuration, the spigot 114a may be a Luer lock type configuration or, a larger lumen diameter may be used for the port member 114, such that the port member 114 is essentially a female port adapted to receive a tube therewithin.

The mask 10 further includes a forehead support 200 that includes an arm 150 coupled to the mask body 100 at a projection 109 that is located at, and extends upwardly from, the apex 105 (i.e. at an apical region) of the mask body 100. The coupling between the arm 150 and the mask body 100, by way of the projection 109, is adapted for providing progressive and controlled pivoting movement of the arm 150 and the forehead support 200 relative to the mask body 100 in a direction transverse to the plane of the face of a patient wearing the mask 10, namely movement of the arm 150 and forehead support 200 in an arc range of motion in the sagittal plane relative to the mask body 100, to thereby provide incremental or infinite adjustment of the forehead support relative to the mask body 100.

The projection 109 preferably comprises two side walls 126 and a rear support wall or web 128. The side walls 126 and/or rear wall 128 of the projection 109 includes at least one reinforcing rib 134 for rigidifying and strengthening the projection 109 to resist torque or moments acting on the at least one projection 109. The arm 150 includes a proximal end 160, near to the mask body 100, a distal end 165 spaced from the mask body 100 for connection with a forehead support member 201 which, as described below, supports a forehead support cushion 400 which engages the patients forehead. An intermediate portion 162 of the arm 150 extends between the proximal end 160 and distal end 165.

The side walls 126 of the projection 109 include a pair of opposite and axially aligned mating grooves or apertures 136 which are adapted to receive a pair of mating protrusions 152 at or near the proximal end 160 of the arm 150. The forehead support member 201 is either pivotally coupled to the distal end 165 of the arm 150 as in the embodiments of FIGS. 1 to 10 and 12 to 30 or is fixed relative to the arm 150 as in the embodiment of FIG. 11. The rear wall 128 of the projection 109 has an opening 130 through which a manually operable thumb screw-like member 1000 that is operable for adjusting the angular displacement of the arm 150 relative to the mask body 100 is located. It is to be appreciated that other devices or assemblies other than a thumb screw 1000 can be employed for manually adjusting the angular displacement of the arm 150 relative to the mask body 100. The thumb screw 1000 includes a knurled knob 1016 and a threaded elongated shaft 1002 extending therefrom. The opening 130 within the rear wall 128 of the projection 109 comprises an annular flange 132 or boss containing a tooth or thread 133 or other suitable engagement means adapted for threaded engagement with a helical thread 1008 disposed at or near a proximal end 1004 of the elongate shaft 1002 of the thumb screw 1000. It will be appreciated that the thread 133 may be a partial thread or a non-continuous thread comprising a plurality of teeth 133. Forming the thread 133 as a non-continuous thread 133 may simplify manufacturing.

The proximal end 160 of the arm 150 is an upside-down U-shape configuration comprising a horizontal web portion and laterally opposite downwardly extending legs 154 defining a U-shaped cavity therebetween. A pair of the first mating protrusions 152 are axially aligned and extend laterally outwardly from outwardly facing sides of the legs 154 at the proximal end 160 of the arm 150 and are adapted to locate within the mating grooves or apertures 136 in the opposite side walls 126 of the projection 109 to thereby allow the arm 150 to pivot as illustrated in FIGS. 8, 9 and 10 about a pivot axis X-X, illustrated in FIGS. 2, 3, 5 and 7, relative to the projection 109 and the body 100. Alternatively, a dowel or rod member (not shown) passes through the legs 154 and the apertures 136 and is fixed therein to allow the arm 15 to pivot about the axis X-X. The interconnection of the protrusions 152 and the apertures 136 acts as an articulation joint, pivot joint or a fulcrum such that when, as described in more detail below, the adjustment means 1000 is manipulated by rotating the knurled knob 1016 to cause the adjustment means to move in an axial direction Y-Y, as illustrated in FIGS. 6, 8, 9 and 10, the arm 150 pivots about the axis X-X in the sagittal plane relative to the mask body 100 when worn, in use, by a patient.

The threaded elongate shaft 1002 of the knurled thumb screw 1000 is adapted to threadably engage the thread 133 within the opening 130 in the rear wall 128 of the projection 109. The U-shaped recess between the legs 154 of the arm 150 receives therewithin the elongate shaft 1002 of the thumb screw 1000. The elongate shaft 1002 of the thumb screw 1000 includes an annular slot 1012 between the thread 1008 on the shaft 1002 and the knurled knob 1016 for receiving and effectively capturing a pair of laterally opposite protrusions 156 extending inwardly from the legs 154 and into the U-shaped recess thereof. As illustrated in FIGS. 8, 9 and 10, rotation of the thumb screw 1000 causes axial displacement of the thumb screw 1000 relative to the threaded opening 130 within the rear wall 128 of the projection 109 in the direction of the axis Y-Y. Because the pair of inwardly extending protrusions 156 are captured within the annular slot 1012 of the thumb screw 1000, rotation of the thumb screw 1000 causes displacement of the protrusions 156 and the legs 154 of the arm 150 substantially in the direction of axial displacement of the thumb screw 1000 relative to the threaded opening 130. As the inwardly extending protrusions 156 are spaced apart from the pair of laterally and outwardly extending protrusions 152, axial movement of the inwardly extending protrusions, as described above, causes the arm 150 to pivot about the outwardly extending protrusions 152 and the pivot axis X-X defined thereby as illustrated in FIGS. 8, 9 and 10.

The above described mechanism for manually adjusting the angular displacement of the arm 150 relative to the mask body 100 is advantageous in that it is relatively compact, involves few separate components and is therefore less expensive and more efficient to manufacture. Also, the components of the above described mechanism are located proximal to the mask body 100 and, as a result, the weight and bulk of the mechanism for manually adjusting the angular displacement of the arm 150 relative to the mask body 100 is located near to the mask body 100. Thus, the mask 10 is more appropriately balanced with more weight distributed more closely towards the mask body 100 which offers benefits in terms of stabilising the mask 10 on a patients face when worn by a patient. Embodiments of the above described mechanism for adjusting the angular displacement of the arm 150 enable more weight to be distributed more closely towards the mask body 100 rather than distally from the mask body 100, such as at a location towards the distal end 165 of the arm 150 which, in contrast to embodiments of the present invention, would result in a more unwieldy mask that would be more prone to movement on the patients face when in use.

Rotation of the thumb screw 1000 causes relatively small movement of the inwardly extending protrusions 156 about the axis X-X relative to the resultant movement caused to the distal end 165 of the arm 150 and the forehead support member 201. Angular increment markings 161 are provided on the outwardly facing sides of the legs 154 at the proximal end 160 of the arm 150. The increment markings 161 are adapted to provide an indication of the angular position of forehead support arm 150 relative to the side walls 126 of the projection 109 by visually observing how many markings 161 are visible above the side walls 126. The markings 161 may assist the user to reset the position of the forehead support arm 150 in the event that it is moved away from the customary or desired position.

Figure 11:
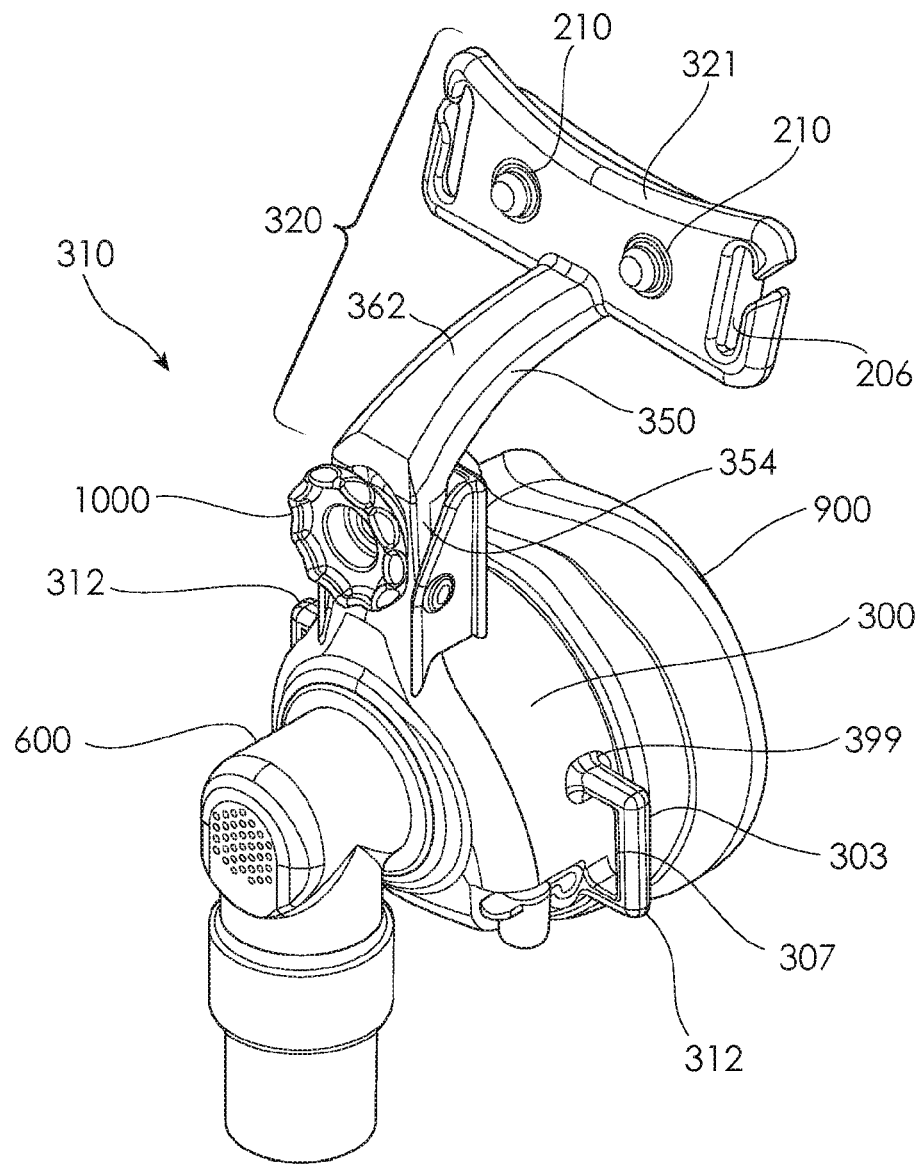
FIG. 11 illustrates a perspective view of a mask in accordance with another embodiment of the invention in which the mask body includes a variation on a pair of transversely opposite headgear anchors adapted for attachment to headgear and in which the arm extending from the mask body and the forehead support member are integrally formed.
Figure 12:
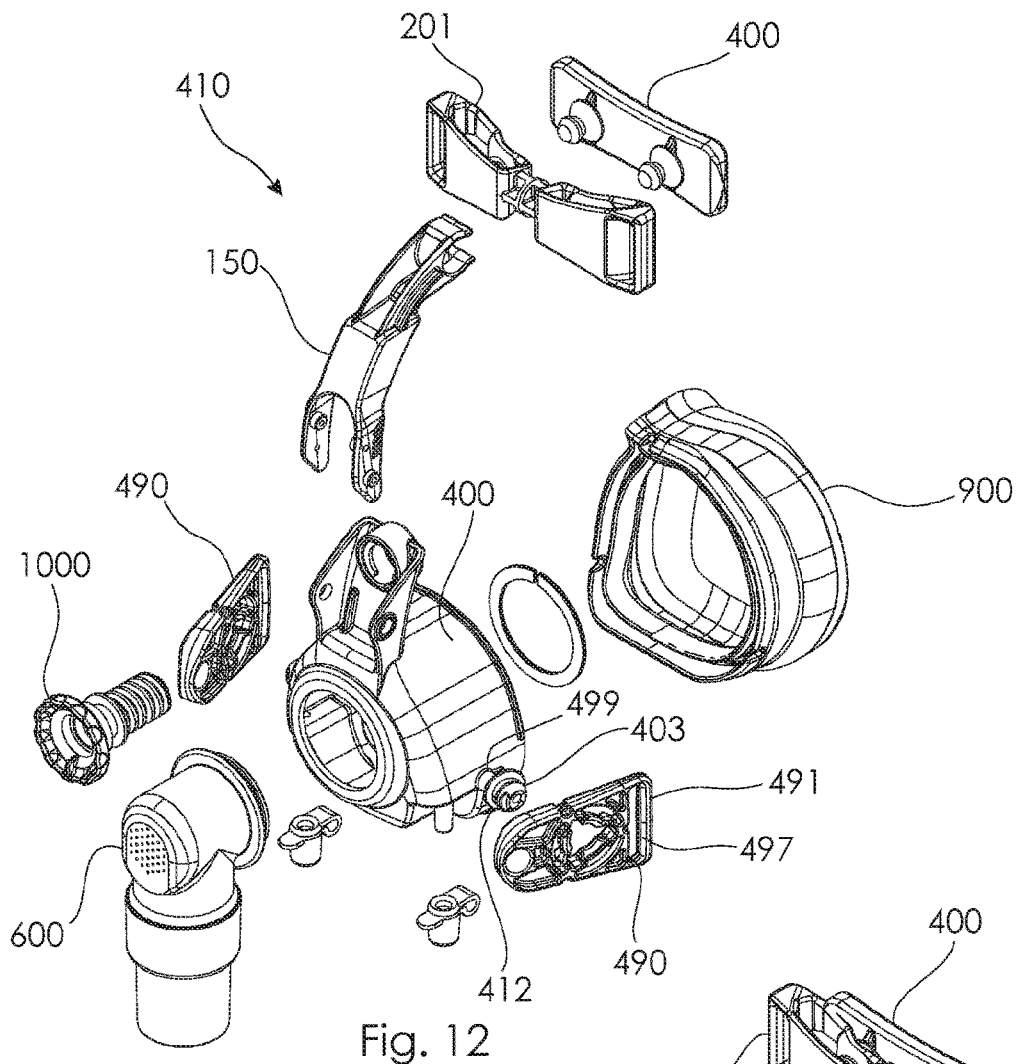
FIG. 12 illustrates an exploded perspective view of another embodiment of the mask in which the mask body includes another variation on a pair of transversely opposite headgear anchors and a headgear attachment device adapted for attachment of headgear to the mask body.
Figure 13:
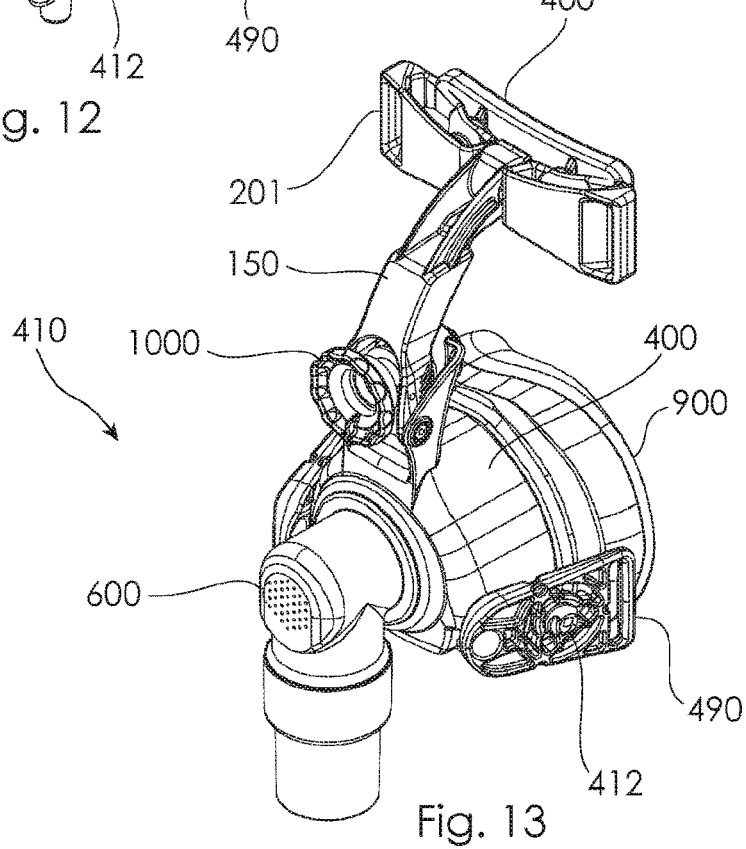
FIG. 13 illustrates a perspective view of the mask of FIG. 12 in which headgear attachment devices are coupled to the headgear anchors.
Figure 14:
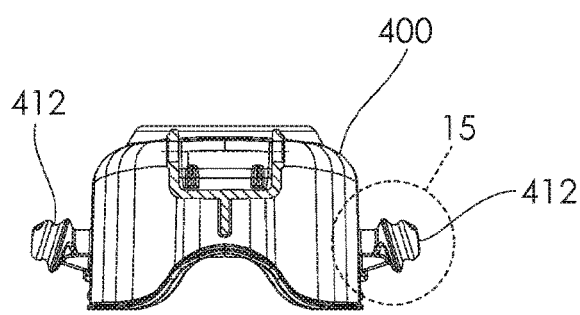
FIG. 14 illustrates a top view of the mask body of the mask of FIG. 12 showing the pair of transversely opposite headgear anchors extending from the mask body.
Figure 15:
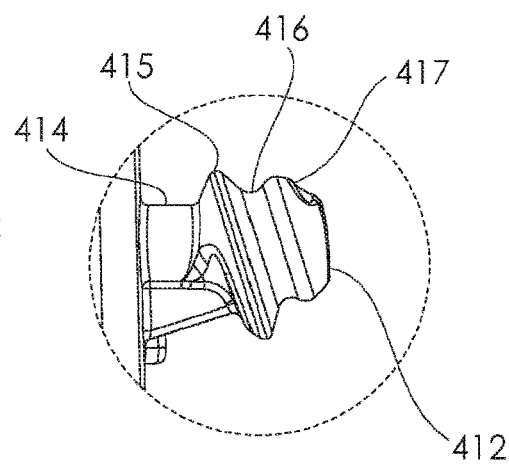
FIG. 15 illustrates a magnified view of one of the pair of transversely opposite headgear anchors of the mask of FIG. 12.

The forehead support member 201 and the arm 150 may be integrally formed, such as in the embodiment of FIG. 11 in which the forehead support 320 includes an integrally formed forehead support member 321 and arm 350, or manufactured as two separate pieces and assembled. The forehead support member 201 comprises at least one wing 202, but preferably comprises two wings 202, 204, which are interconnected by the rod 205. If the forehead support member 201 comprises a single wing, the arm 150 is disposed off-centre or angled relative to the mask body 100 (not shown). In the illustrated embodiments, the arm 150 is centred between the wings 202, 204. The wings 202, 204 may comprise at least one forehead headgear anchor 206 adapted to receive headgear for securing the mask 10 to a patients face. Each forehead anchor 206 may be an aperture, such as a D-shape or C-shape, or another shape of aperture or cavity suitable as a means for allowing a piece of headgear to be attached thereto. The illustrated forehead anchors 206 comprise a headgear slot or entry point 208 as shown in FIGS. 5 and 7, which allows a piece of headgear to be attached to the forehead anchor 206 by hooking or threading a loop of the headgear into the aperture. In another embodiment, the forehead support comprises a single forehead anchor 206 disposed generally near the centre of the forehead support member 201 (not shown).

FIGS. 8, 9 and 10 illustrate a range of angular displacement through which the arm 150 and forehead support member 201 can move relative to the pivot axis X-X. Preferably the range of angular displacement is up to about 60 degrees and preferably up to about 50 degrees. Different ranges of movement may be achieved by spacing the outwardly extending protrusions 152 and the inwardly extending protrusions 156 at different intervals apart from each other.

The rear wall 128 of the projection 109 includes a pair of laterally spaced apart ribs 134. The ribs 134 are adapted to limit the inwards deflection of the legs 154 at the proximal end 160 of the arm 150 towards the rear wall 128 as might occur if the thumb screw 1000 is over-adjusted when the arm 150 and forehead support member 201 of the forehead support 200 is in the extreme forward position as shown in FIG. 8. By providing a limit to the inwards deflection of the legs 154 the ribs 134 can prevent the disengagement of protrusions 152 from the apertures 136 in the projection 109 of the mask body 100, and the undesired separation of the forehead support 200 from the mask body 100.

In the embodiments illustrated in FIGS. 1 to 10 and 12 to 30, the forehead support member 201 is a separate member from the arm 150. The distal end 165 of the arm 150 includes a recess 166 that is adapted to receive a rod portion 205 of the forehead support member 201 in a snap fit arrangement that allows for pivotal movement of the forehead support member 201 relative to the arm 150. Lateral ribs 167 near the distal end 165 of the arm 150 limit the range of rotation of the forehead support member 201 within the recess 166 to define a range of pivotal motion thereof and stop the forehead support member 201 from rotating to a position in which the forehead support cushion 400 faces away from the patients forehead. When configured with a mask and/or head gear, the forehead support member 201 can be adjusted relative to the arm 150 to provide better alignment with the patient's forehead. In the embodiment of FIG. 11, the forehead support 320 includes an integrally formed forehead support member 321 and arm 350. The legs 354 of the arm 350 extend at an angle to the intermediate portion 362 and the intermediate portion 362 extends at an angle relative to the forehead support member 321. Thus, the legs 354 may be angularly offset or substantially parallel relative to the forehead support member 321 to provide a more secure and comfortable anatomical fit between the patient and the mask 310. In the embodiment illustrated in FIG. 11, the forehead support member 321 has the forehead cushion 400 coupled thereto. The forehead cushion 400 is tapered to provide a comfortable anatomical fit between the patient and the forehead support 200, 320.

Referring to FIGS. 25*a* and 25*b*, at least one, preferably two openings 210 are formed on the forehead support member 201 for receiving at least a portion of a forehead cushion 400. Optionally, the openings 210 comprise a tapered face 212 on at least one side which may assist with placement of the forehead cushion 400 and/or such that the forehead cushion 400 may only be inserted into the forehead support 200 in one direction. This is of benefit for patients adjusting the device in dimly lit or unlit conditions or who have poor eyesight.

FIGS. 23*a*, 23*b* and 23*c* illustrate the forehead cushion 400 in more detail. The forehead cushion 400 comprises two protrusions 402 which releasably mate with the openings 210 in the forehead support member 201. The forehead cushion 400 is preferably made from a soft polymer material, for example silicone or another suitable bio-compatible polymer, such that the forehead cushion 400 provides a more comfortable fit for a patient using the mask 10. Optionally, the headed protrusions 402 may be inwardly or outwardly canted. When the forehead cushion 400 is mounted on the forehead support member 201, the forehead cushion 400 is substantially perpendicular relative to the arm 150 albeit pivotal relative to the arm 150 through a range of motion afforded by the pivotal coupling between the forehead support member 201 and the arm 150. The forehead cushion 400 comprises a base 404 that is substantially aligned with the coronal plane when the mask 10 is worn by a patient for contact with the patient's forehead. Each protrusion 402 includes a head 406 with a substantial cone shape with a rounded tip, or a barb shape, which has a larger diameter than the openings 210 such that once forced through the openings 210 resists withdrawal therefrom.

In a further embodiment, the protrusions 402, or elsewhere on the forehead cushion 400, may comprise other or further predetermined shapes or features, such as the frustoconical portion 407 positioned between the head 406 and a mask facing surface 403 of the cushion 400. The frustoconical portion 407 is adapted to space the forehead support member 201, in particular a central region thereof, apart from the mask facing surface 403 of the forehead cushion 400. Thus, the connection between the forehead cushion 400 and the forehead support member 201 provided by the protrusions 402, formed of flexible material, in conjunction with the spacing apart of the mask facing surface 403 of the cushion 400 from the forehead support member 201 allows a fine movement of the forehead cushion 400 of the forehead support 200 relative to the mask 10. This feature allows for further flexibility of the orientation of the forehead cushion 400 relative to the patients forehead to improve comfort for the patient wearing the mask 10. The forehead cushion 400 has rounded or contoured edges 410 for additional comfort while wearing the mask 10. The protrusions 402 comprise buttresses 412 for reinforcing and stabilise the support formations 404.

The face cushion 900 is adapted to space the mask body 100 away from the patient's face and to provide a seal between the patient and the mask body 100 in as comfortable a manner as possible. The face cushion 900 has a flange 902 and a lip portion 906 that abuts with the rim 108 of the mask body 100. The lip portion 906 of the face cushion 900 includes three cut away portions 908 which are adapted to substantially align with corresponding mating members on the mask body 100. The lip portion 906 may be formed with an outer lip wall 907a and an inner lip wall 907b for receiving the rim 108 of the mask body 100 therebetween. The face cushion 900 has at least two distinctive regions. The first region may be a relatively softer region than that of the second region, which may be provided by forming the first region with a reduced wall thickness than that of the second region. The first region may be adapted to elastically deform to allow a comfortable fit on a patients face and may provide an improved gas tight seal. The face cushion 900 has a number of frosted, opaque or semi-transparent sections which may define a gripping portion used to improve the grip of a user or clinician on the face cushion to facilitate easier removal or placement of the face cushion 900 or may provide a higher or lower friction to improve sealing or comfort between the patient and the face cushion, in use. The face cushion 900 comprises three distinctive regions, a first region 912, a second region 914 and a third region 916, which vary in thickness and rigidity.

The elbow or swivel 600 of the mask 100 of FIG. 1 is illustrated in more detail in FIGS. 24a to 24d and includes a first pivotal coupling 602 and second pivotal coupling 604 wherein the axis of rotation of the pivotal couplings 602, 604 are substantially perpendicular to allow a tube or conduit (not shown) to be attached to the elbow 600 to rotate and move relative to the mask body 100. The first and second pivotal couplings 602, 604 are gas tight. Alternatively, the first and second pivotal couplings 602, 604 may be articulation couplings that each allow for movement in more than one axis. The elbow 600 comprises a swivel head portion 606 and an elongate tubular portion 608. Swivel head portion 606 is adapted to be received by the gas inlet aperture 110 of the mask body 100. The elongate tubular portion 608 is in fluid communication with the swivel head portion, such that when a conduit or tube is connected to the elbow 600, a breathable gas may be delivered to the cavity of the mask body 100. The longitudinal axis of the elongate tubular portion 608 is perpendicular, about 90 degrees, relative to the swivel head portion 606 although other angles may also be used. The first snap pivot coupling 602 of the swivel head portion 606 is preferably attached to the gas inlet aperture 110 of the mask body 100 and is retained in the gas inlet aperture 110 by a retaining means, such as a circlip 609.

A vent array 660 is disposed on the head portion 606 of the elbow 600 and comprises of a plurality of vent holes 663 which are depicted in a grid forming a substantially hexagonal arrangement as seen in the FIGS. 24a to 24c in particular. In the illustrated embodiment, there are 36 vent holes in the vent array 660 which are uniformly spaced in a triangular grid spaced approximately 2.1 mm apart. However, the vent holes 613 are preferred to have a 1 mm to 1.5 mm minimum spacing. The vent holes 613 are preferably flared or fluted passages extending from a proximal opening 666, as illustrated in FIG. 24b, located nearer the patients face when worn to a distal opening 664, illustrated in FIGS. 24a and 24c, located further from the patient's face. The passage of each vent hole 613 tapers from the proximal opening 666, which has a larger diameter, to the distal opening 664, which has a smaller diameter, as is illustrated in the front and rear views of FIGS. 24a and 24b respectively. The tapering vent holes 613 are advantageous as they attenuate or muffle the sound of the patient's breathing during use. The vent holes 613 may be disposed in one or more other predetermined arrays or arrangements (i.e. not in the illustrated hexagonal arrangement), however the vent holes 613 preferably have a total combined area of the distal openings 664 area of about 9 mm$^2$ to about 11 mm$^2$, but more preferably the area is about 10.1 mm$^2$. The total combined area of the proximal openings 666 of the vent holes 613 is about 15 mm$^2$ to about 21 mm$^2$, or more preferably about 18 mm$^2$. Such a vent array can also assist in retaining fluids, particularly water vapour, within the mask 10 to assist the patient in retaining fluids during use. Further, the vent holes 613 may be tapered between 0.1 to 10 degrees from their central axes, or may have a standard tapering of around 1 degree from their central axes. The vent holes 613 may have a different shape for the distal and proximal openings 664, 666. For example the inner proximal openings 666 may be hexagonal and the distal openings 664 may be circular or vice versa. Changing the shape of the vent holes 613 can enhance the sound attenuation or muffling effect of the vent holes 613 and may also increase compliance with a prescribed therapy.

Referring to FIG. 1, the second snap pivot coupling 604 of the elongate tubular portion 608 is preferably attached to a conduit adaptor portion 618, which may be removably engaged with the elongate tubular portion 608 of the elbow 600 and be adapted for fluid communication therewith. The conduit adaptor portion 618 may be adapted to mate with the snap fit pivot coupling 604 and form a gas tight seal. A conduit or tube (not shown) may then be engaged with the conduit adaptor portion 618 to supply a breathable gas to a patient. The conduit adaptor portion 618 may be tapered to accommodate gas conduits of varying sizes, which may allow the mask of the present disclosure to be used with a number of different devices.

Figure 19:
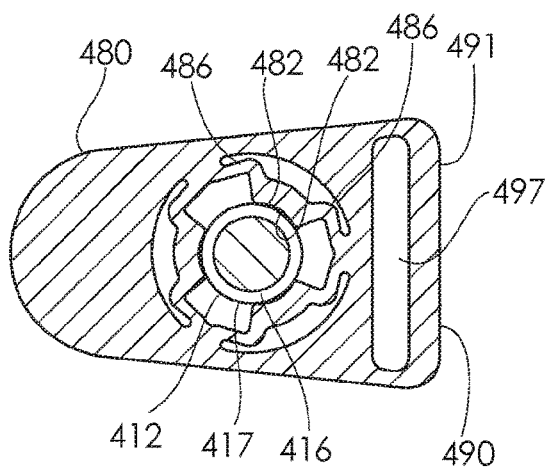
FIG. 19 illustrates a side view of a transverse cross section of the headgear attachment device of the mask of FIG. 12 illustrating the attachment device disengaged from the headgear anchor.
Figure 20:
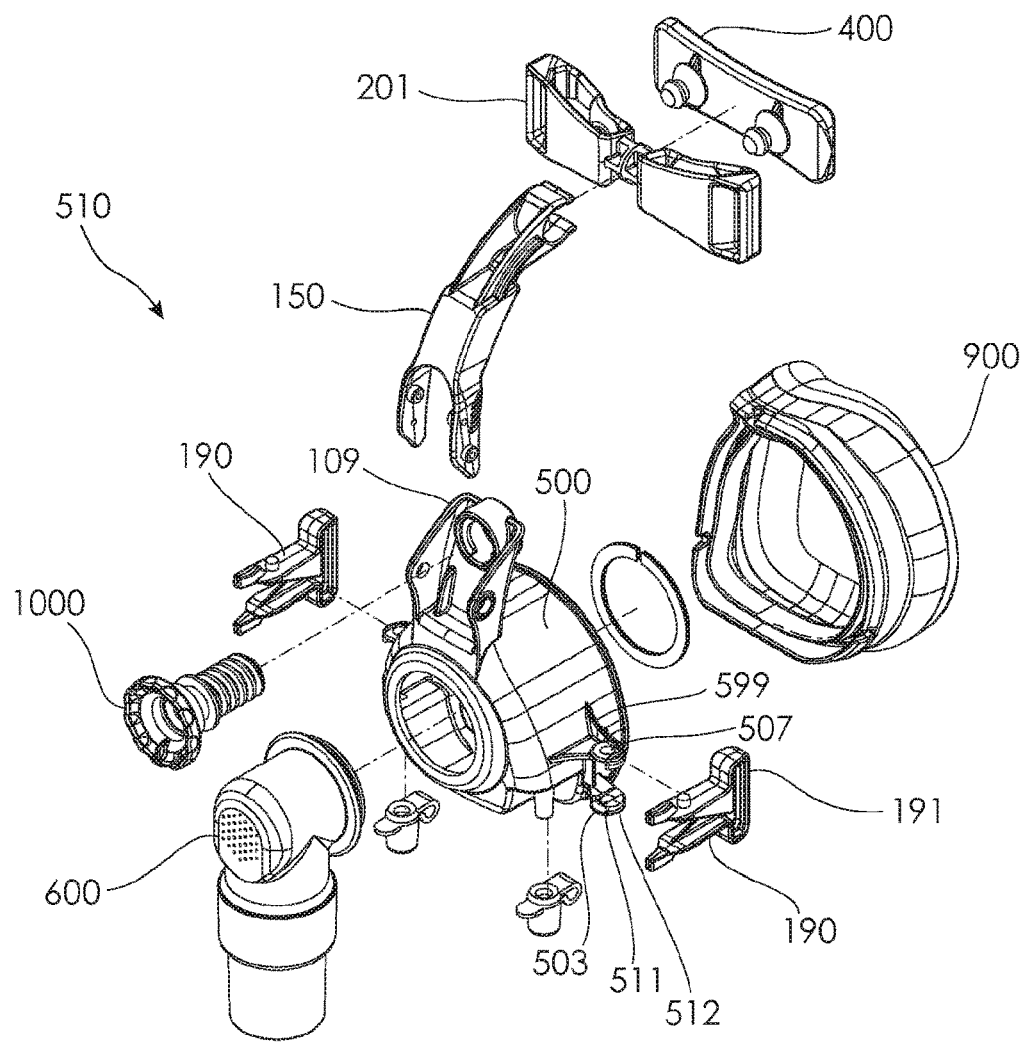
FIG. 20 illustrates an exploded perspective view of another embodiment of the mask in which the mask body includes another variation on a pair of transversely opposite headgear anchors and a headgear attachment device adapted for attachment of headgear to the mask body.
Figures 21, 22:
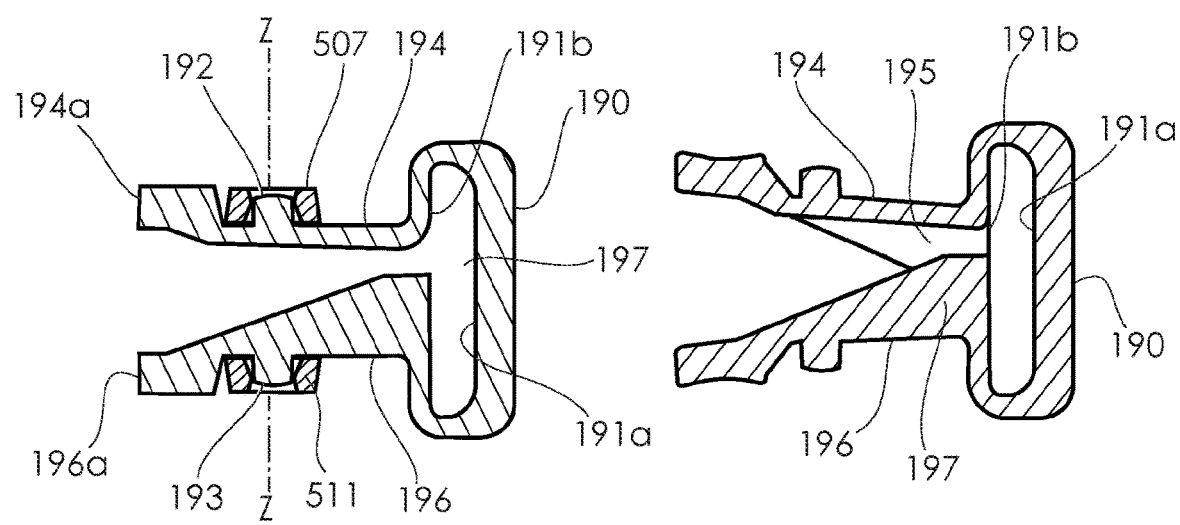
FIG. 21 illustrates a side view of a median section of the headgear anchor coupled with the headgear attachment device of the mask of FIG. 20.
FIG. 22 illustrates a side view of a median section of the headgear attachment device of the mask of FIG. 20

FIGS. 1 to 10 illustrate an embodiment of mask 10 in which the body 100 includes a pair of transversely opposite headgear anchors 112 adapted for attachment to headgear (not shown) that a patient wears during use to secure the mask 10 to the patients face to achieve a gas tight seal. The headgear may be fabricated from an elastomeric fabric, or other material suitable to position the mask to a desired region of the face of the patient. The headgear anchors 112 protrude from the mask body 100 substantially transversely outwardly therefrom and are adapted for connection with headgear (not shown). FIG. 11 illustrates another embodiment of the mask 310 in which the mask body 300 includes a variation on the pair of transversely opposite headgear anchors 312 adapted for attachment to headgear (not shown). FIGS. 12 to 19 illustrate another embodiment of the mask 410 in which the mask body 400 includes another variation on the pair of transversely opposite headgear anchors 412 adapted for attachment to a headgear attachment device 490. FIGS. 20 to 22 illustrate yet another embodiment of the mask 510 in which the body 500 includes yet another variation of the pair of transversely opposite headgear anchors 512 adapted for attachment to a headgear attachment device 190. In an embodiment, not shown in the figures, the anchors 512 may be adjustable relative to the body 500 to achieve a more comfortable anatomical fit or a more secure gas tight fit.

Referring to the embodiment illustrated in FIGS. 1 to 10, the headgear anchors 112 have a proximal end 99, near to the mask body 100, and a distal end 103 projecting away from the mask body 100. Each one of the anchors 112 consists of a loop that defines an aperture 107 for receiving a variety of headgear attachment devices (not shown) or for directly receiving a loop portion of an elastomeric fabric strip comprising the headgear (not shown). In other embodiments, such as the embodiment illustrated in FIG. 11, the anchors 312 may be a loop that defines a single aperture 307 for receiving a variety of headgear attachment devices (not shown) or for directly receiving a loop portion of an elastomeric fabric strip comprising the headgear (not shown).

FIG. 11 illustrates another embodiment of the mask 310 in which the mask body 300 includes a variation on the pair of transversely opposite headgear anchors 312 adapted for attachment to headgear (not shown). The pair of transversely opposite headgear anchors 312 have a proximal end 399, near to the mask body 300, and a distal end 303 projecting away from the mask body 300. The distal end 303 of the headgear anchor 312 defines an aperture 307 for receiving a loop portion of an elastomeric fabric strip comprising the headgear (not shown).

Referring to the embodiment illustrated in FIGS. 12 to 19, the headgear anchors 412 each include a shaft member 414 having a proximal end 499, near to the mask body 400, and a distal end 403 projecting away from the mask body 400. The shaft member 414 includes a canted radially outwardly facing annular slot 416 defined by a proximal canted annular ridge 415 and an axially spaced apart and canted annular distal ridge 417. The term canted, as used herein, refers to the slot 416 and ridges 415, 417 extending in a direction at an angular deviation (i.e. slope) from a vertical or horizontal plane which in the illustrated embodiment is at an angle between an axial plane of the shaft member 414 and a plane perpendicular to the axial plane.

The headgear attachment device 490 includes a body 480 including a loop 491 at one longitudinal end thereof that defines an aperture 497 for receiving a loop portion of an elastomeric fabric strip comprising the headgear (not shown). The body 480 contains a substantially centrally located mating opening 482 surrounded by a plurality of radially spaced apart and inwardly extending ramps 484 that are each adapted to move radially inwardly and outwardly to respectively define relatively smaller and larger diameter states of the mating opening 482. The inwardly extending ramps 484 are each supported by resiliently flexible support members 486 that operate to support the ramps 484 relative to the surrounding body 480 and to bias the ramps 484 radially inwardly such that the resting location of the ramps 484 is radially inwardly thereby defining the smaller diameter state of the mating opening 482, which is illustrated in FIG. 18.

Figure 18:
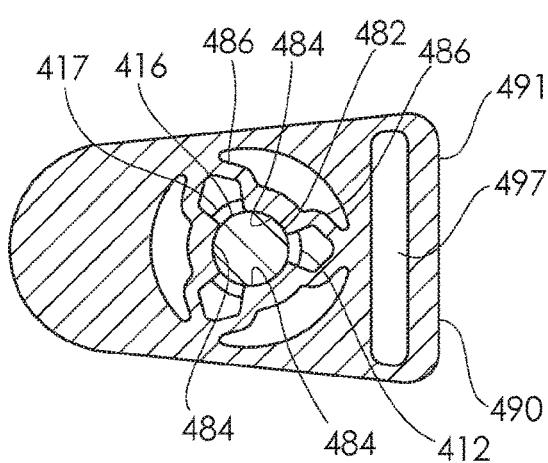
FIG. 18 illustrates a side view of a transverse cross section of the headgear attachment device of the mask of FIG. 12 illustrating the attachment device engaged with the headgear anchor.

FIG. 18 illustrates the headgear attachment device 490 engaging the headgear anchor 412 engaging the wherein the shaft member 414 of the headgear anchor 412 is received within the mating opening 482 within the body 480 of the headgear attachment device 490. The ramps 484 are maintained in their radially inward resting location by the resilient support members 486 located within the annular slot 416 of the headgear anchor 412. Removal of the headgear attachment device 490 from the headgear anchor 412 is achieved by levering the headgear attachment device 490 relative to the headgear anchor 412 such that one or more the ramps 484 engage a distally located portion of the proximal canted annular ridge 415 to thereby lever one or more of the ramps 484 over a proximally located portion of the distal canted annular ridge 417. The diameter of proximal annular ridge 415 is sized to be greater than the diameter of the distal annular ridge 417. The radial displacement of the ramps 484 (i.e. their maximum radially outward location) is such that they cannot pass over the larger diameter proximal annular ridge 415 to a location on the shaft member 414 immediately adjacent the mask body 400.

Figure 16:
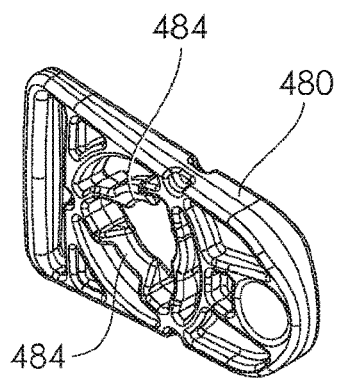
FIGS. 16 and 17 illustrate perspective and side views of the headgear attachment device of the mask of FIG. 12.
Figure 17:
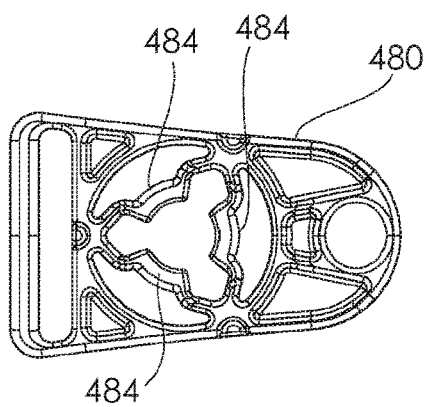

The headgear attachment device 490 can then be separated from the headgear anchor 412 once at least one or more of the ramps 484 has cleared the distal canted annular ridge 415. Alternatively, removal of the headgear attachment device 490 from the headgear anchor 412 can be achieved by simply pulling the headgear attachment device 490 in an axial direction away from the headgear anchor 412 such that one or more of the ramps 484 pass over the distal canted annular ridge 417. As the ramps 484 pass over the distal canted annular ridge 417 they are forced radially outwardly to clear the distal annular ridge 417 as illustrated in FIG. 19. Connecting the headgear attachment device 490 to the headgear anchor 412 involves pressing the headgear attachment device 490 axially towards the headgear anchor 412 such that one or more the ramps 484 pass over the distal canted annular ridge 417 and locate within the canted radially outwardly facing annular slot 416. FIGS. 16 and 17 illustrate how the ramps 484 of the headgear attachment device 490 are tapered or chamfered to allow them to pass over the distal annular ridge 417 when the headgear attachment device 490 is pressed onto or pulled from the headgear anchor 412.

Referring to the embodiment illustrated in FIGS. 20 to 22, the headgear anchors 512 have a proximal end 599, near to the mask body 500, and a distal end 503 projecting away from the mask body 500. The distal ends 503 of the anchors 512 each include a pair of spaced apart and axially aligned apertures 507, 511 which are engaged by the head gear attachment device 190 as illustrated in FIG. 21 and described below. The headgear attachment device 190 includes a loop 191 that defines an aperture 197 for receiving a loop portion of an elastomeric fabric strip comprising the headgear (not shown). The loop 191 has a closed end 191*a* and an open end 191*b*. At the open end 191*b*, the loop 191 includes a pair of legs 194, 196 which extend transversely from the loop 191. The legs 194, 196 are coupled to the loop 191 such that the legs 194, 196 are adapted to pivot relative to the loop 191 and relative to each other in a median plane through both of the longitudinally extending legs 194, 196. Thus, the legs 194, 196 move relative to each other in a scissor-like motion. The legs 194, 196 are biased towards an initial resting position such that the legs 194, 196 can be manually or otherwise forced towards each other and once the force is removed the legs 194, 196 spring back to their initial resting position. The legs 194, 196 have respective free ends 194*a*, 196*a* and include axially aligned and opposite protrusions 192, 193 located at a position between the loop 191 and the free ends 194*a*, 196*a*. Thus, as the legs 194, 196 are forced together in the above described scissor-like motion the protrusions 192, 193 also move towards each other such that they can fit within a space between the pair of spaced apart and axially aligned apertures 507, 511 at the distal ends 103 of the headgear anchors 112. When the protrusions 192, 193 are aligned with the apertures 507, 511 and the force moving the legs 194, 196 towards each other is removed the legs 194, 196 are biased towards their initial resting position and the protrusions 192, 193 engage the apertures 507, 511 to thereby engage the headgear attachment device 190 with one of the anchors 512. The apertures 507, 511 are tapered to guide the protrusions 192, 193 into the apertures 507, 511. To disengage the headgear attachment device 190 from one of the anchors 512 the legs 194, 196 are forced together so that the protrusions 192, 193 clear the apertures 107, 111 and the device 190 can be separated from the anchor 512. When the device 190 is in engagement with the anchor 512 the device 190 can pivot relative to the mask body 500 about an axis defined Z-Z by the axes of the apertures 107, 111 and the protrusions 192, 193, as illustrated in FIG. 21. FIG. 22 illustrates an embodiment of the headgear attachment device 190 including gussets 195, 197 that reinforce the legs 194, 196.

Figure 31:
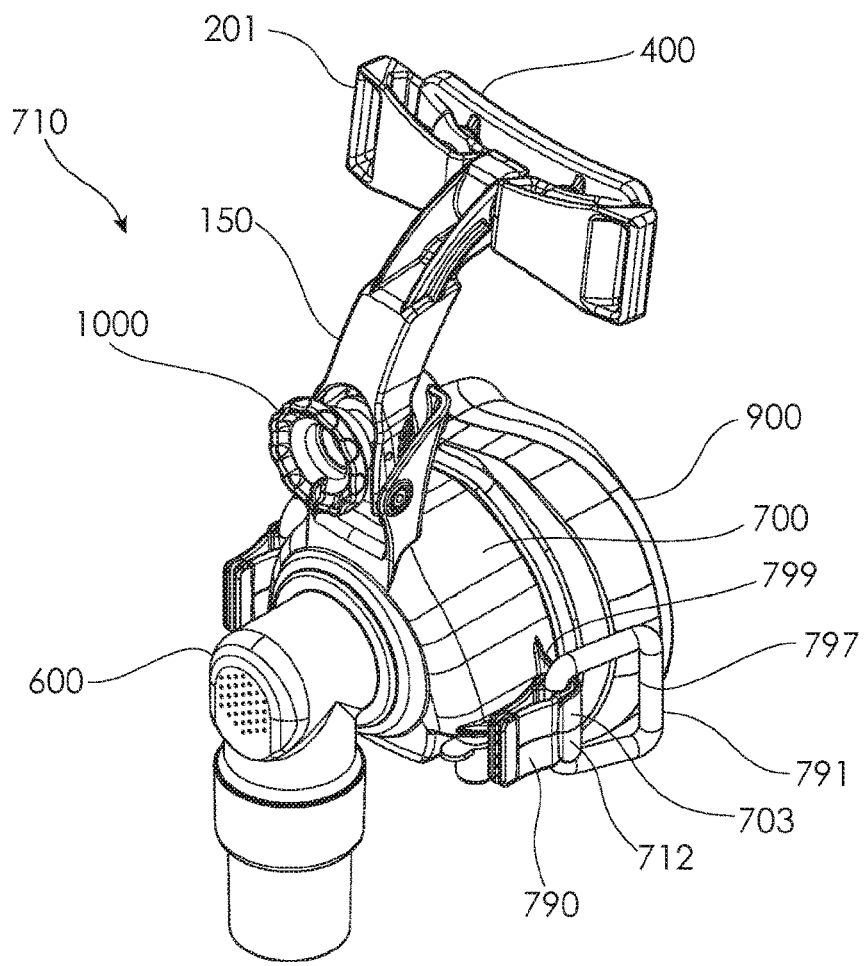
FIG. 31 illustrates a perspective view of another embodiment of the mask in which the mask body includes another variation on a pair of transversely opposite headgear anchors and a headgear attachment device adapted for attachment of headgear to the mask body.
Figure 32:
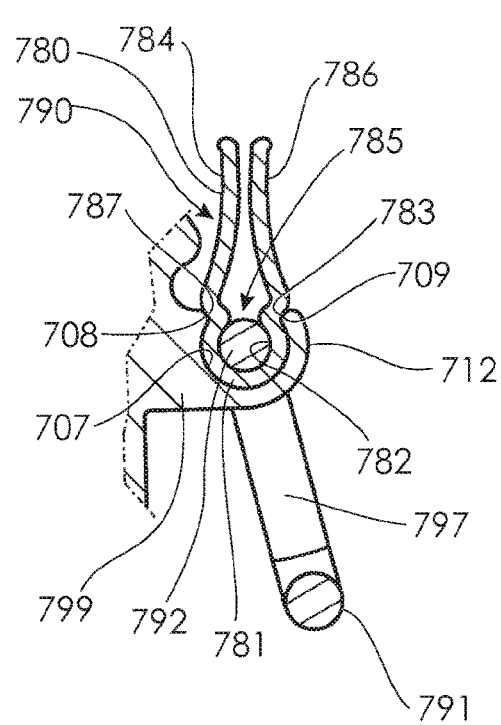
FIGS. 32 and 33 illustrate a plan view of a transverse section of the headgear anchor and headgear attachment device of the mask of FIG. 31.
Figure 33:
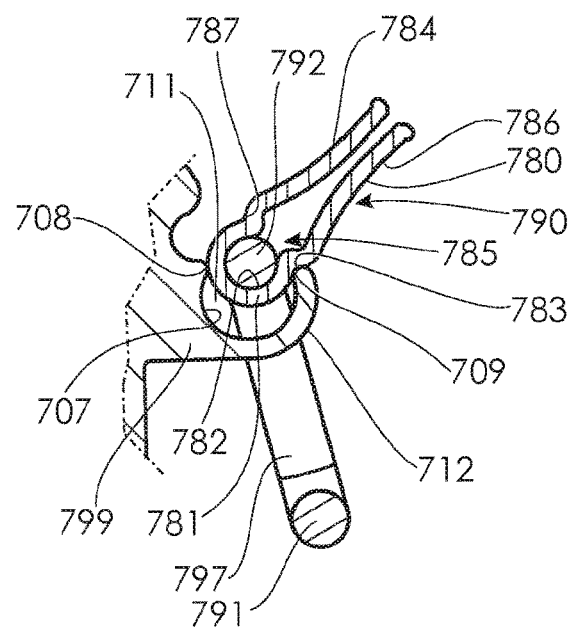

Referring to the mask 710 of FIGS. 31 to 33, the mask body 700 includes headgear anchors 712 including a proximal end 799, near to the mask body 700, and a distal end 703 projecting away from the mask body 700. As can be seen in FIGS. 32 and 33, which illustrate enlarged plan views of a transverse section of one of the headgear anchors 712, the distal end 703 of the anchor 712 includes an arcuate slot 707 including a proximal lip 708 and a distal lip 709 that define an opening 711 therebetween facing posteroanteriorly (i.e. away from the patient's face when in use) which is engaged by the head gear attachment device 790 as illustrated in FIGS. 31 to 33 and described below. The headgear attachment device 790 is comprised of a clip member 780 and a loop member 791 that, in the illustrated embodiment, are formed separately. The loop member 791 is preferably made of plastic or metal and defines an aperture 797 for receiving a loop portion of an elastomeric fabric strip comprising the headgear (not shown). The clip member 780 has a rounded web 781 and two spaced apart legs 784, 786 extending therefrom. The rounded web 781 defines an internal slot 782 adapted to receive an elongated portion 792 of the loop member 791. Junctions between the web 781 and the legs 784, 786 taper inwardly towards each other to define a narrow waist region 785 for retaining the elongated portion 792 of the clip member 780 within the internal slot 782.

The rounded web 781 of the clip member 780 is adapted to be inserted into the arcuate slot 707 of the anchor 712 in a snap-fitting engagement whereby the proximal and distal lips 708, 709 are adapted to locate within indentations 787, 783 formed in an outer surface of the clip member 780 at the waist region 785 between the web 781 and the legs 784, 786. Disengagement of the clip member 780 from the anchor 712 is achieved, as illustrated in FIG. 33, by manually forcing the legs 784, 786 outwardly away from the mask body 700 to thereby pivot the clip member 780 within the slot 707. Such pivoting of the clip member 780 within the slot 707 levers the rounded web 781 out of the slot 707 about a fulcrum where the distal lip 709 is located within one of the indentations 783 at the waist region 785.

Figures 26, 27:
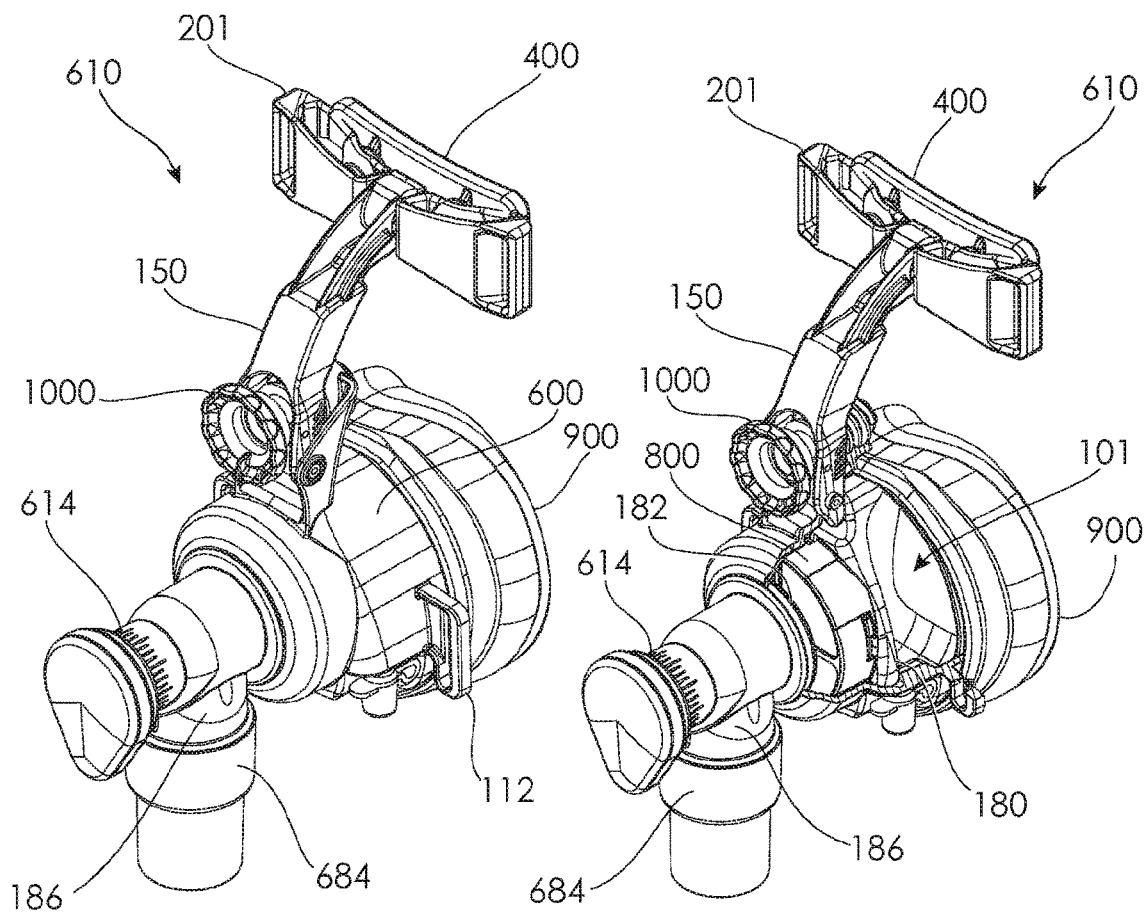
FIG. 26 illustrates a perspective view of a mask in accordance with another embodiment of the invention including an HME (heat and moisture exchanger) element cartridge.
FIG. 27 illustrates a perspective view of the mask of FIG. 26 in which parts of the mask body are cut away to reveal location of the HME element cartridge within the mask body.
Figure 28:
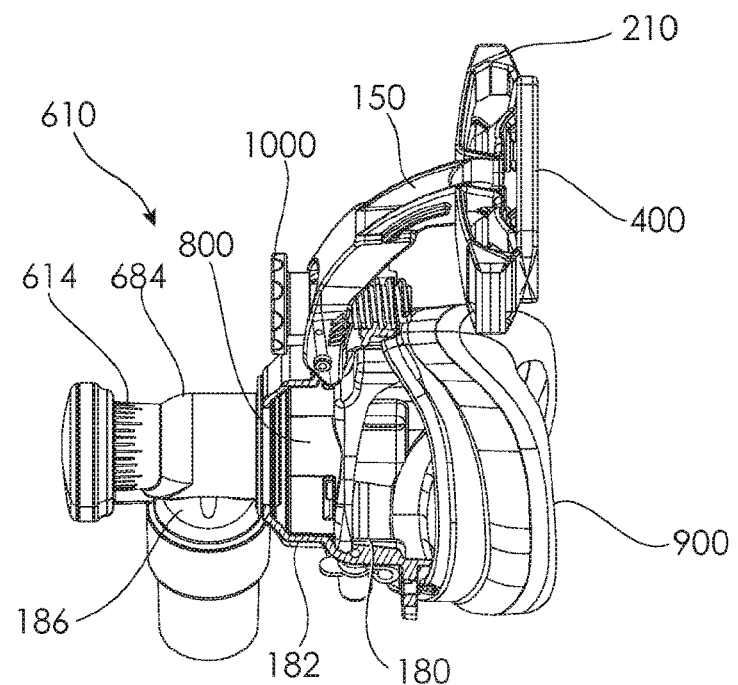
FIG. 28 illustrates a perspective view from above of the mask of FIG. 26 in which parts of the mask body are cut away to reveal location of the HME element cartridge within the mask body.
Figure 29:
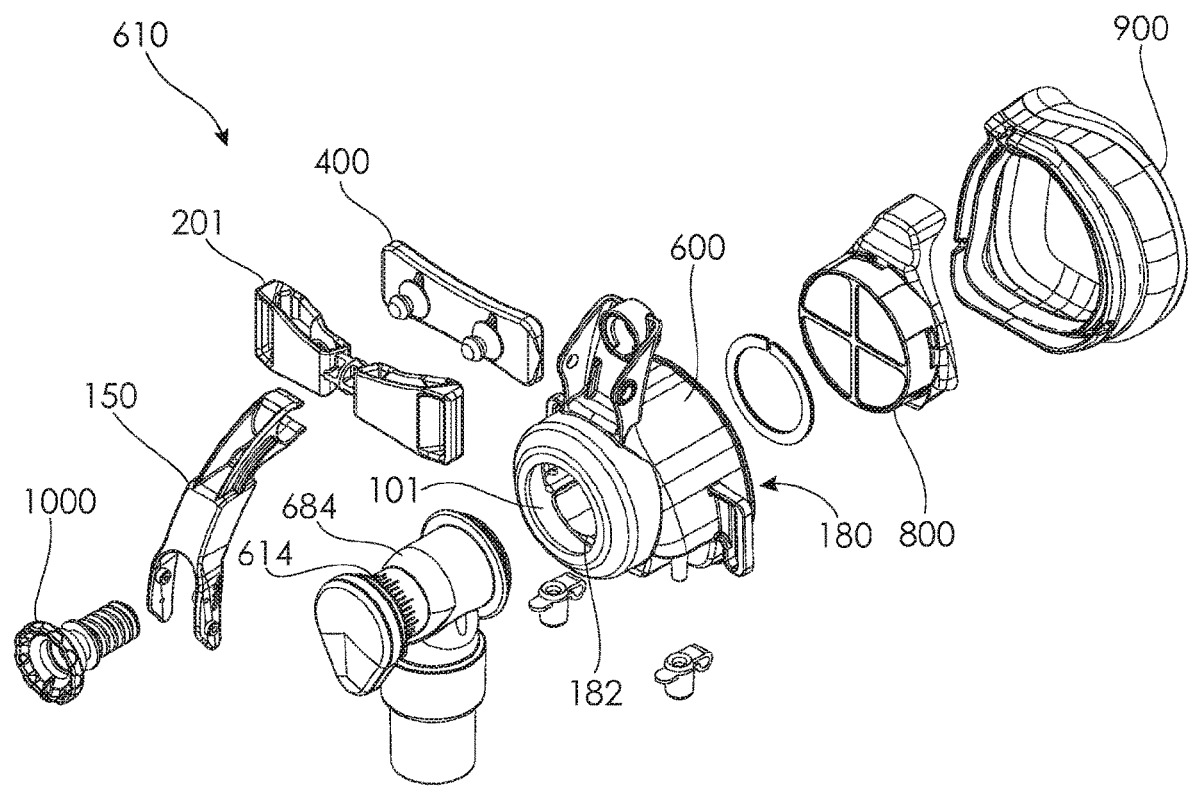
FIG. 29 illustrates an exploded perspective view of the mask including the HME element cartridge of FIG. 26.

FIGS. 26 to 30 illustrate another embodiment of the mask 610 which is similar to the embodiment of FIGS. 1 to 10 with the exception that it also includes an HME element cartridge 800 comprising the HME housing 802 and HME element 814. FIGS. 27 and 28 illustrate perspective views of the mask 610 with parts of the mask body 600 cut away to reveal location of the HME element cartridge 800 within the mask body 600. The HME cartridge 800 is positioned in the mask body 600 but in an alternate embodiment (not shown) the HME cartridge 800 or at least an HME element 814 may be located between the elbow 600 and the gas conduit, or in the elbow 600. It is to be appreciated that the other embodiments of the mask 10, 310, 410, 510, 710 disclosed herein could be used, with or without modification, with the HME cartridge 800 or HME element 814. The mask 610 is similar in configuration to the mask 10 illustrated in FIGS. 1 to 10 and FIG. 11, such that it may be used for a positive pressure therapy regime, and like reference numerals are used to identify like features. The mask 610 comprises a mask body 600 wherein the mask cavity 101 is comprised of a first cavity 180 located proximally to the patients face when in use and a substantially cylindrically shaped second cavity 182 located adjacent and distally relative to the first cavity 180. As shown in FIGS. 27 and 28, the HME cartridge 800 is locatable within the second cavity 182 abutting against the interior of the front wall 106 of the mask body 600. In the embodiment of FIGS. 26 to 30, the HME cartridge 800 is positioned relatively close to the plane of the patients face when in use, such that a significant percentage of moisture from a patient's breathing may be retained and directed back towards the patient during use. This embodiment of the mask 610 may result in the patient losing less fluids during sleep and may increase compliance to a prescribed therapy regime.

The distally located second cavity 182 of the mask body 600 adjoins the inlet aperture 110 at the front of the mask body 610. Exhaled gas is directed towards the HME cartridge 800 such that moisture in the exhaled gas can be at least partially captured by the HME element 814 of the HME cartridge 800. Breathable gas from a CPAP or NIPPV device is directed through the HME cartridge 800 and at least a portion of the moisture that is retained by the HME element 814 from the previous exhalation is inhaled by the patient, which assists the patient in retaining fluids.

The mask 610 includes a modified elbow 684 including an array of longitudinally extending and parallel vent slots 614. The modified elbow 684 comprises an end region 186 that is operable to direct the flow of gas from a CPAP or NIPPV device through the aperture 110 in the front of the mask body 600 and into the second cavity 182. Another embodiment of the modified elbow 684 could include a thermistor (not illustrated) which determines the temperature of the gas from a CPAP or NIPPV device directed into the mask 610.

The modified elbow 684 is described in further detail in U.S. patent application Ser. No. 13/518,553 and is incorporated herein by reference.

Existing HME elements are fabricated from a polymeric material which is of sufficient size to capture moisture from a patients breath. However, these polymer HME elements are generally bulky and render the mask uncomfortable to wear. As illustrated in FIGS. 27 to 30, the HME cartridge 800 disclosed herein is more compact than existing HME element or element cartridges. In the embodiment disclosed herein, the HME element 814 is comprised of a coated cardboard or paper material, or alternatively, a foam element or a sponge type element which may be tightly wound to allow capture and temporary retention of moisture. The more compact size of the presently disclosed HME element 814 and cartridge 800 allows the HME cartridge to be positioned nearer to a patients face while still maintaining a sufficient level of comfort for the patient in use.

Figure 30:
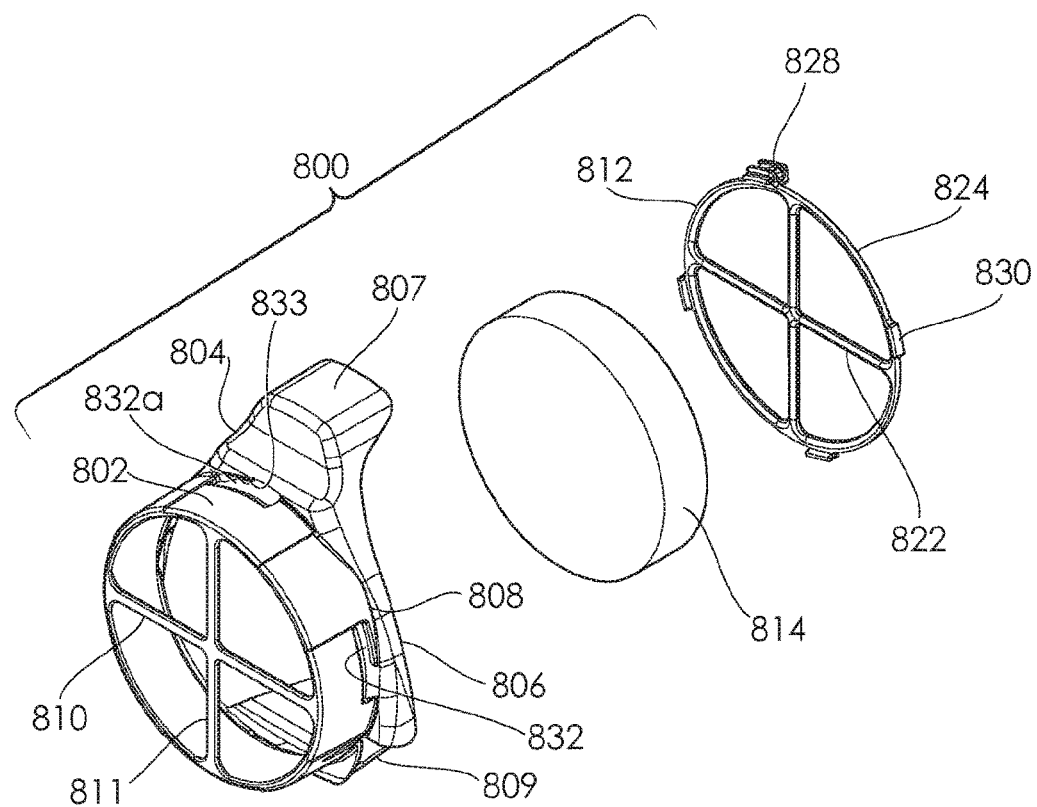
FIG. 30 illustrates an exploded perspective view of the HME element cartridge of the mask of FIG. 26.

Referring to FIG. 30, the HME cartridge 800 is comprised of an HME housing 802 removably attached to a mask support frame 804. The mask support frame 804 and the HME housing 802 are adapted to be releasably retained within the mask 610. The mask support frame 804 includes a substantially round main body 806 including arms 807 and 809 extending rearwardly from the top and bottom of the main body 806 of the frame 804. The main body 806 of the mask support frame 804 comprises an HME housing aperture 808 adapted to receive the HME housing 802 and the HME element 814 therewithin. The top arm 807 is adapted to be received in an upper portion of the mask body 100 and the bottom arm 809 is adapted to be received in a lower portion of the mask body 100. Arms 807 and 809 may further be retained between the inner cushion lip 907b and the mask body 100 to thereby restrict rearwards motion of the HME cartridge 800 into the first cavity 180 of the mask body 600. The mask support frame 804 preferably conforms to a shape or contour of the interior of the mask body 600 within the second cavity 182 portion such that the mask support frame 804 takes up a minimal space within the mask 610. The HME cartridge 800 is retained, at least in part, in the mask body 600 by the face cushion 550. Alternatively, or in addition, the HME cartridge 800 is retained in the mask body 600 by an interference fit between the mask support frame 804 and the internal surface of the mask body 600.

The HME housing 802 is cylindrical and is adapted to fit snugly within the complementarily shaped second cavity 182 when the element cartridge 800 is installed within the mask body 600. Thus, the HME housing 802 is disposed in the second chamber 182 and the mask support frame 804 is disposed in the first chamber 180 of the mask body 600.

The HME housing 802 comprises a first web 810 and a second web 812 that are axially spaced apart and adapted to capture the HME element 814 by sandwiching the cup-shaped, or alternatively disc shaped, HME element 814 therebetween to retain the HME element 814 in the HME housing 802. The second web 812 engages a distal side of the HME element 814 and the first web 810 engages a proximal side. One or both the first web 810 and the second web 812 are releasably coupled to the HME housing 802 to install and retain the HME element 814 therebetween. In the illustrated embodiment, the second web 812 comprises ramped lugs 830 which extend radially outwardly from the annular support member 824 and are adapted to engage corresponding ramped slots 832 in the housing 802 in a bayonet coupling fashion and a locking means 828 to interlock and engage in a snap fit fashion with a detent protuberance 833 of a corresponding ramped slot 832a in the HME housing 802. Thus, the second web 812 is inserted into the housing 802 and rotated to engage the ramped lugs 830 with the ramped slots 832 to thereby couple the second web 812 to the housing 802 in a bayonet fitting to resist both axial and radial separation therebetween. The locking means 828 engages the corresponding ramped slot 832a, which differs from the rest of the ramped slots 832 in that it has an additional detent protuberance 833, in a snap fit or the like to resist rotation of the second web 812 relative to the housing 802. It will be appreciated that in an alternative embodiment, the first web 810 is attachable and the second web 812 is fixed to the HME housing 802 or the first and second webs may both be integrally formed with the HME housing 802.

The first web 810 is comprised of a cross-hair like structure 811 supported by the HME housing 802 at one end within a passage defined within the HME housing 802. The second web 812 includes an annular support member 824 supporting a crosshair-like structure 822 that, when coupled to the HME housing 802 sandwiches a centre portion of the HME element 814 between the cross hair structures 811, 822 of the first and second webs 810, 812.

The crosshair-like structures 811, 822 of the first and second webs 810, 812 may be aligned with each other or angularly offset at an angle of up to 90 degrees, say 45 degrees. In the illustrated embodiment, the first web 810 is integrally formed with the cylindrical HME housing 802 whereas the second web 812 is secured within the HME housing 802 with the HME element 814 sandwiched therebetween.

The mask support frame 804 is adapted to be removed from the mask body 600 such that the HME element housing 802 and HME element 814 can be separated from the mask support frame 804 and replaced with an unused HME element housing 802 and HME element 814. Alternatively, the HME element 814 can be replaced and the HME element housing 802 can be reused. The mask support frame 804 and the replacement HME housing 802 and HME element 814 are reassembled and replaced in the mask body 600. The HME housing 802 may be releasably coupled to the mask support frame 804 by any suitable means. In the illustrated embodiment, a bayonet coupling is used to secure the HME housing 802 to the mask support frame 804.

All of the embodiments of the mask 10, 310, 410, 510, 610 and 710 illustrated herein include the forehead engagement member 200 or 320, however, it is to be appreciated that the present disclosure also envisages an alternative form of each of the masks 10, 310, 410, 510, 610 and 710 that omits the forehead engagement member 200 or 320. Accordingly, the present disclosure also includes any one of the respiratory masks 10, 310, 410, 510, 610 and 710 disclosed herein and including a mask body 100, 300, 400, 500, 600 and 700 including a base or lower wall 102 and two side walls 104 upstanding from the lower wall 102 that converge to form an apex 105 and a pair of transversely opposite headgear anchors adapted for attachment to headgear that a patient wears during use to secure the mask to the patients face in accordance with any one of the embodiments disclosed in the figures and described above. Accordingly, in such forms the respiratory mask omits the forehead engagement member 200, 320.

It will be appreciated that the terms fluid, gas, breathable gas and air may be used interchangeably. The term air may include a mixture of oxygen and nitrogen or any other breathable gas which may be delivered to a patient. Optionally, the breathable gas may include a medicament.

Although the disclosure has been described with reference to specific examples, it will be appreciated by those skilled in the art that the disclosure may be embodied in many other forms, in keeping with the broad principles and the spirit of the disclosure described herein.

What is claimed is:

1. A respiratory mask, comprising:
a mask body including a base and walls upstanding from the base and converging towards an apical region;
a forehead engagement member coupled to the mask body and including an arm, which is pivotally coupled to the apical region of the mask body and extends therefrom so that the arm is movable relative to the mask body in a sagittal plane when the mask body is worn by a patient; and
an adjustment mechanism for adjusting the relative positions of the arm and the mask body, wherein the adjustment mechanism is located in the region of the pivotal coupling between the arm and the apical region of the mask body and includes a manual operable member that is adapted for movement in an axial direction relative to the mask body.

2. The respiratory mask of claim 1, wherein the arm extends from the apical region of the mask body to a forehead region of a patient when in use.

3. The respiratory mask of claim 1, wherein a portion of the forehead engagement member is captured by the manually operable member whereby movement of the manually operable member in the axial direction relative to the mask body is configured to adjust the position of the forehead engagement member relative to the mask body.

4. The respiratory mask of claim 1, wherein the manually operable member includes a threaded shaft that is threadably coupled to a threaded aperture at the apical region of the mask body.

5. The respiratory mask of claim 2, wherein a distal end of the arm is pivotally coupled to a forehead support member for pivotal movement of the forehead support member relative to the arm.

6. The respiratory mask of claim 5, wherein the forehead support member comprises a forehead cushion removably coupled thereto for contacting a patient's forehead, wherein a main body of the forehead cushion is supported in relation to the forehead support member.

7. The respiratory mask of claim 1, wherein the mask body includes a pair of gas ports that are disposed outwardly and downwardly facing recesses on laterally opposite sides within the base of the mask body.

8. The respiratory mask of claim 7, wherein each of the gas ports includes a spigot extending downwardly within a respective one of the recesses, each spigot including an axial lumen for fluid communication between an internal cavity of the mask body and a conduit coupled to the spigot.

9. The respiratory mask of claim 1, wherein an elbow shaped swivel gas conduit extends from a front of the mask body and includes a vent array comprising a plurality of vent holes tapering from a larger diameter proximal opening to a smaller diameter distal opening.

10. A respiratory mask, comprising:
a mask body including a base and walls upstanding from the base and converging towards an apical region;
a forehead engagement member extending from the apical region of the mask body;
the forehead engagement member coupled to the mask body so as to be movable relative to the mask body in a sagittal plane when the mask body is configured to be worn by a patient; and
an adjustment mechanism for adjusting the relative positions of the forehead engagement member and the mask body;
wherein the mask body includes a pair of transversely opposite headgear anchors adapted for attachment to a headgear configured to be worn by the patient to secure the mask to the patient's face, further wherein the headgear anchors each include a shaft having a proximal end near the mask body and a distal end projecting away from the mask body, the shaft member including a radially outwardly facing slot adapted to receive a portion of a headgear coupling, wherein the radially outwardly facing slot is annular and canted and is defined by a proximal canted annular ridge and an axially spaced apart and canted annular distal ridge, wherein the slot and the proximal and distal ridges are canted relative to an axial plane of the shaft member and a plane perpendicular to the axial plane.

11. The respiratory mask of claim 10, wherein each of the headgear anchors is adapted for snap fit engagement with a headgear coupling.

12. The respiratory mask of claim 11, wherein the headgear coupling includes an aperture adapted to receive the headgear anchor and a resiliently displaceable engagement member within the aperture adapted to engage the headgear coupling.

13. The respiratory mask of claim 12, wherein the resiliently displaceable engagement member includes one or more radially inwardly extending ramps supported within the aperture by resiliently flexible support members adapted to bias the ramps in a radially inwards direction.

14. The respiratory mask of claim 1, further including a heat and moisture exchanger removably locatable within a cavity defined within the mask body.

15. The respiratory mask of claim 14, wherein the heat and moisture exchanger is removably locatable between a cavity defined within the mask body and a lip, flange or other feature of the cushion.

16. The respiratory mask of claim 1, wherein the body includes a pair of transversely opposite headgear anchors adapted for attachment to a headgear that a patient wears during use to secure the mask to the patient's face.

* * * * *